US011913039B2

(12) United States Patent
Godawat et al.

(10) Patent No.: US 11,913,039 B2
(45) Date of Patent: Feb. 27, 2024

(54) METHOD FOR PRODUCING RECOMBINANT ALKALINE PHOSPHATASE

(71) Applicant: Alexion Pharmaceuticals, Inc., Boston, MA (US)

(72) Inventors: Rahul Godawat, Woodbridge, CT (US); Meghan Dewitt, Madison, CT (US); Siguang Sui, South Glastonbury, CT (US); Saravanamoorthy Rajendran, Long Valley, NJ (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 314 days.

(21) Appl. No.: 17/043,464

(22) PCT Filed: Mar. 13, 2019

(86) PCT No.: PCT/US2019/022102
§ 371 (c)(1),
(2) Date: Sep. 29, 2020

(87) PCT Pub. No.: WO2019/190752
PCT Pub. Date: Oct. 3, 2019

(65) Prior Publication Data
US 2021/0317425 A1  Oct. 14, 2021

Related U.S. Application Data

(60) Provisional application No. 62/650,583, filed on Mar. 30, 2018.

(51) Int. Cl.
C12N 9/16 (2006.01)
C07K 1/22 (2006.01)
C12N 5/071 (2010.01)
C12P 21/00 (2006.01)

(52) U.S. Cl.
CPC .............. *C12N 9/16* (2013.01); *C07K 1/22* (2013.01); *C12N 5/0682* (2013.01); *C12P 21/005* (2013.01); *C12Y 301/03001* (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Luo et al. (HAL Open Science, 2015, pp. 1-18).*
Ali et al., "Isolation and characterization of calcifying matrix vesicles from epiphyseal cartilage," Proc Natl Acad Sci USA. 67(3):1513-20 (1970).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).

(Continued)

*Primary Examiner* — Hope A Robinson
(74) *Attorney, Agent, or Firm* — Clark & Elbing LLP

(57) ABSTRACT

A method of producing recombinant alkaline phosphatase comprising control of production parameters, particularly harvest clarified culture fluid (HCCF) and filtration pool (UFDF), to provide a defined total sialic acid content.

22 Claims, 12 Drawing Sheets

Specification includes a Sequence Listing.

(56) References Cited

U.S. PATENT DOCUMENTS

| | | |
|---|---|---|
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,650,412 B2* | 5/2017 | Konstantinov .... B01D 15/3809 |
| 9,650,413 B2* | 5/2017 | Konstantinov ...... C12N 9/2402 |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 10,603,361 B2 | 3/2020 | Odrljin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0015784 A1 | 1/2016 | Shaw et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |
| 2019/0099473 A1 | 4/2019 | Fujita et al. |
| 2020/0282012 A1 | 9/2020 | Francois |
| 2021/0169994 A1 | 6/2021 | Voegtli et al. |
| 2021/0317425 A1* | 10/2021 | Godawat .................. C12N 9/16 |
| 2022/0154155 A1* | 5/2022 | Godawat ............... C12P 21/005 |

FOREIGN PATENT DOCUMENTS

| | | |
|---|---|---|
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 1985697 A1 | 10/2008 |

(56) References Cited

FOREIGN PATENT DOCUMENTS

| | | |
|---|---|---|
| EP | 2158319 | 3/2010 |
| EP | 1759001 B1 | 4/2011 |
| EP | 2158319 B1 | 12/2011 |
| EP | 3250227 A2 | 12/2017 |
| JP | 8-70875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO 2005/105156 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO 2018/164995 | 9/2018 |
| WO | WO-2021/081026 A1 | 4/2021 |
| WO | WO-2021/119218 A1 | 6/2021 |

OTHER PUBLICATIONS

Anderson et al., "The role of matrix vesicles in growth plate development and biomineralization," Front Biosci. 10:822-37 (2005).

Beertsen et al., "Root development in mice lacking functional tissue non-specific alkaline phosphatase gene: Inhibition of acellular cementum formation," J Dent Res. 78(6):1221-1229 (1999) (10 pages).

Bennett et al., "Extracellular domain-IgG fusion proteins for three human natriuretic peptide receptors," J Biol Chem. 266(34):23060-23067 (1991).

Bernard, "Ultrastructural localization of alkaline phosphatase in initial intramembranous osteogenesis," Clin Orthop Relat Res. 135:218-225 (1978).

Bonilla, "Pharmacokinetics of immunoglobulin administered via intravenous or subcutaneous routes," Immunol Allergy Clin N Am. 28:803-819 (2008).

(56) References Cited

OTHER PUBLICATIONS

Byers et al., "Effect of enzyme replacement therapy on bone formation in a feline model of mucopolysaccharidosis type VI," Bone. 21(5):425-431 (1997).
Cameron et al., "Minireview: Natriuretic peptides during development of the fetal heart and circulation," Endocrinology. 144(6):2191-2194 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for European Patent Application No. 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, "Investigation of the role of FcRn in the absorption, distribution, and elimination of monoclonal antibodies," Dissertation: State University of New York at Buffalo, 2007 (Abstract only) (2 pages).
Greenberg et al., "A homoallelic $Gly^{317}$ to Asp mutation in ALPL causes the perinatal (lethal) form of hypophosphatasia in Canadian Mennonites," Genomics. 17:215-217 (1993).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in $Akp2^{-/-}$ mice," J Bone Miner Res. 21(9):1377-1386 (2006).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & Peptide Drug Delivery—Third International Conference: Minimally invasive delivery methods, Sep. 22-23, Philadelphia, PA, USA," IDrugs. 6(11):1043-5 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millan, *Mammalian Alkaline Phosphatases: From Biology to Applications in Medicine and Biotechnology*, Wiley-VCH Verlag GmbH & Co., Weinheim, Germany (2006) (324 pages).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516, <www.ncbi.nlm.nih.gov/protein/AAF64516>, retrieved Apr. 16, 2013 (2 pages).
NCBI Protein Database Accession No. AAC33858, <www.ncbi.nlm.nih.gov/protein/AAC33858>, retrieved Apr. 16, 2013 (1 page).
NCBI Protein Database Accession No. AAH21289, <www.ncbi.nlm.nih.gov/protein/AAH21289>, retrieved Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321(Pt 2)(Pt 2):297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharm Res. 14(7): 911-6 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33(2):405-412 (1983).
Wang et al., "A mouse model for achondroplasia produced by targeting fibroblast growth factor receptor 3," Proc Natl Acad Sci USA. 96(8):4455-4460 (1999).

(56) References Cited

OTHER PUBLICATIONS

Wang et al., "Structure-based chemical modification strategy for enzyme replacement treatment of phenylketonuria," Mol Genet Metab. 86(1-2):134-140 (2005).
Weiss et al., "A missense mutation in the human liver/bone/kidney alkaline phosphatase gene causing a lethal form of hypophosphatasia," Proc Natl Acad Sci USA. 85(20):7666-7669 (1988).
Whyte et al., "Enzyme-replacement therapy in life-threatening hypophosphatasia," N Engl J Med. 366(10):904-13 (2012).
Whyte et al., "Markedly increased circulating pyridoxal-5'-phosphate levels in hypophosphatasia," J Clin Invest. 76(2):752-756 (1985).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Zierhut et al., "Population PK-PD model for Fc-osteoprotegerin in healthy postmenopausal women," J Pharmacokinet Pharmacodyn. 35(4):379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 37(2):309-17 (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacia hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int. 60(3):309-15 (1997).
Ciancaglini et al., "Contribution of matrix vesicles and alkaline phosphatase to ectopic bone formation," Braz J Med Biol Res. 39(5):603-10 (2006).
Crawley et al., "Enzyme replacement therapy in a feline model of Maroteaux-Lamy syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).

Guo et al. "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Millan et al., "Enzyme replacement therapy for murine hypophosphatasia," J Bone Miner Res. 23(6):777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically $^{32}$P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte, "Hypophosphatasia," in The Metabolic and Molecular Bases of Inherited Disease (8th ed.), pp. 5313-5329, 2001 (McGraw-Hill Book Company) (epub pp. 1-41).

(56) References Cited

OTHER PUBLICATIONS

Whyte, Chapter 18: Heritable Forms of Rickets and Osteomalacia. *Connective Tissue and Its Heritable Disorders*. Wiley-Liss, Inc., eds. R.M. Royce and B. Steinmann, 765-87 (2002).
Whyte et al., "Marrow cell transplantation for infantile hypophosphatasia," J Bone Miner Res. 18(4):624-36 (2003).
Yamamoto et al., "Prolonged survival and phenotypic correction of Akp2$^{-/-}$ hypophosphatasia mice by lentiviral gene therapy," J Bone Miner Res. 26(1):135-42 (2011).
Communication from Examining Division for European Application No. 05739065.0, dated Jun. 18, 2009 (6 pages).
Communication from Examining Division for European Application No. 05739065.0, dated Jun. 11, 2010 (5 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Supplementary European Search Report for European Application No. 05739065, dated Dec. 2, 2008 (3 pages).
Choe et al., "Substrate profiling of cysteine proteases using a combinatorial peptide library identifies functionally unique specificities," J Biol Chem. 281(18):12824-12832 (2006).
Official Action and Translation for Japanese Application No. 2013-544989, dated Oct. 27, 2015 (6 pages).
Harris, "The human alkaline phosphatases: what we know and what we don't know," Clin Chim Acta. 186:133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, dated Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).
Advisory Action for U.S. Appl. No. 11/484,870, dated Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," Am J Pathol. 164(3):841-7 (2004).
Barranger et al., "Lessons learned from the development of enzyme therapy for Gaucher disease," J Inherit Metab Dis. 24(Suppl. 2):89-96 (2001).
Bobé et al., "Fas-mediated liver damage in MRL hemopoietic chimeras undergoing lpr-mediated graft-versus-host disease," J Immunol. 159:4197-4204 (1997).
Boskey, "Amorphous calcium phosphate: The contention of bone," J Dent Res. 76:1433-1436 (1997).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).
Cleland et al., "Emerging protein delivery methods," Curr Opin Biotechnol. 12:212-219 (2001).
Communication from Examining Division for European Application No. 08757088.3, dated Apr. 20, 2011 (4 pages).
Data Sheet for pFUSE-SEAP-hFC "Plasmid designed for the expression of a SEAP-Fc Fusion protein," Invivogen, San Diego, CA (1 page) (1989).
Extended European Search Report for European Application No. 11774253.6, dated Oct. 14, 2013 (8 pages).
Extended European Search Report for European Application No. 11000196.3, dated Jun. 22, 2011 (6 pages).
Extended European Search Report for European Application No. 11004496.3, dated Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Ikezawa, "Glycosylphosphatidylinositol (GPI)-anchored proteins," Biol Pharm Bull. 25(4):409-17 (2002).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
Kasugai et al., "Selective drug delivery system to bone: small peptide (Asp)$_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231(1):1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).

(56) References Cited

OTHER PUBLICATIONS

Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated Jul. 16, 2013 (3 pages).
Patti et al., "Critical residues in the ligand-binding site of the *Staphylococcus aureus* collagen-binding adhesin (MSCRAMM)," J Biol Chem. 270(20):12005-11 (1995).
Reply to Final Office Action for U.S. Appl. No. 13/071,445, dated Oct. 25, 2012 (14 pages).
Reply to Final Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Supplementary European Search Report for European Application No. 08757088, dated Jun. 7, 2010 (5 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).

Whyte, "Hypophosphatasia and the role of alkaline phosphatase in skeletal mineralization," Endocr Rev. 15(4):439-461 (1994).
Whyte, "Chapter 70: Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Science. 290(5491):471-3 (2000).
Skolnick et al., "From genes to protein structure and function: novel applications of computational approaches in the genomic era," Trends Biotechnol. 18(1):34-9 (2000).
The Japanese Journal of Dermatology. 115(6): 843-7 (2005) (11 pages).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(6):847-857 (1998).
Furuya et al., "Structural requirements of C-type natriuretic peptide for elevation of cyclic GMP in cultured vascular smooth muscle cells," Biochem Biophys Res Commun. 183(3):964-969 (1992).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol Cell Physiol. 270:C1311-18 (1996) (9 pages).
Horton et al., "Achondroplasia," Lancet. 370:162-72 (2007).
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).

(56) References Cited

OTHER PUBLICATIONS

Millan, Chapter 7: The in vivo role of TNAP. Mammalian alkaline phosphatases: From Biology to Applications in Medicine and Biotechnology. Wiley-VCH Verlag GmbH & Co., 107-185 (2006).
Miyazawa et al., "Cyclic GMP-dependent protein kinase II plays a critical role in C-type natriuretic peptide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31(1):101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274(5295):2082-2086 (1996).
Potter et al., "Natriuretic peptides, their receptors, and cyclic guanosine monophosphate- dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223(1):1-6 (1996).
Takano et al., "Molecular evolution of shark C-type natriuretic peptides," Zoolog Sci. 11(3):451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319(2):171-178 (2008).
Tsuji et al., "A loss-of-function mutation in natriuretic peptide receptor 2 (Npr2) gene is responsible for disproportionate dwarfism in cn/on mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Whyte, Chapter 207: Hypophosphatasia. *The Online Metabolic and Molecular Bases for Inherited Disease.* McGraw-Hill Book Company, Valle et al. (eds.) (2001) (41 pages).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab-/- mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Chapter 4: Immunoglobulins: Structure and Function," *Microbiology and Immunology On-line,* University of South Carolina School of Medicine, <pathmicro.med.sc.edu/mayer/IgStruct2000.htm> (2009) (12 pages).
Yasoda et al., "Overexpression of CNP in chondrocytes rescues achondroplasia through a MAPK-dependent pathway," Nat Med. 10(1):80-86 (2004).

EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
Extended European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal pancraniosynostosis in a patient with infantile hypophosphatasia," Cleft Palate Craniofac J. 53(6):741-4, doi: 10.1597/15-027 (2016).
International Search Report and Written Opinion for International Patent Application No. PCT/US2015/058498, dated Jan. 22, 2016 (12 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Product Monograph, Including Patient Medication Information. Strensiq™ (asfotase alfa), Solution for Injection 40 mg/mL & 100 mg/mL," <alexionpharma.ca/documents/Strensiq-PM-asfotase-alfa-14Aug2015.aspx>, prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
Center for Drug Evaluation and Research, "Application No. 125513Orig1s000," <www.accessdata.fda.gov/drugsatfda_docs/nda/2015/125513Orig1s000MedR.pdf>, review completed Oct. 20, 2015; retrieved on Jun. 1, 2016 (254 pages).
International Search Report and Written Opinion for International Patent Application No. PCT/US2016/025721, dated Aug. 17, 2016 (18 pages).
Invitation to Pay Additional Fees for International Patent Application No. PCT/US2016/015366, dated Jun. 1, 2016 (7 pages).
Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).
Highlights of Prescribing Information for Strensiq™ (asfotase alfa) Injection, Alexion Pharmaceuticals, Inc., <www.alexion.com/Documents/strensiq_pi-10-2015.aspx> (2015) (19 pages).
Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).
"View of NCT02235493 on Nov. 19, 2015" ClinicalTrials.gov archive, updated Nov. 19, 2015, retrieved Jan. 27, 2017 (4 pages).
Hofmann et al., "Improvement in bone manifestations and respiratory status in infants and young children with HPP treated with asfotase alfa: an update on the ENB-010-10 trial," 7th International Conference on Children's Bone Health, June 27-30, Salzburg, Austria. Bone Abstracts. 4:OC18 (2015) (3 pages).
Epps, "Application No. 125513Orig1s000 Medical Review(s)," Center for Drug Evaluation and Research, <www.accessdata.fda.gov/drugsatfda_docs/nda/2015/125513Orig1s000MedR.pdf>, Oct. 20, 2015 (254 pages).

(56) References Cited

OTHER PUBLICATIONS

International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, dated Oct. 9, 2015 (101 pages).
Reply Brief as Filed in U.S. Appl. No. 12/638,527, dated Apr. 22, 2016 (4 pages).
Examiner's Answer to Appeal Brief for U.S. Appl. No. 12/638,527, dated Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, March 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, April 1-4, Boston, MA. Abstract OR26-3 (2016) (2 pages).
International Search Report and Written Opinion for International Patent Application No. PCT/US2017/025590, dated Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts," J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Wickramasinghe et al., "A case of hypophosphatasia," Ceylon Med J. 48(3):94-5 (2003) (2 pages).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, dated Aug. 10, 2017 (10 pages).
International Search Report and Written Opinion for International Patent Application No. PCT/US2017/047527, dated Nov. 6, 2017 (10 pages).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2016).
Bloch-Zupan, "Hypophosphatasia: diagnosis and clinical signs - a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl-/-mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26):1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).
Mornet et al., "Hypophosphatasia," GeneReviews. www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).

(56) References Cited

OTHER PUBLICATIONS

Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 Å resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
European Collection of Authenticated Cell Cultures (ECACC), General Cell Collection: NS0, Catalogue No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).

Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Chapter 15: Recombinant enzyme replacement therapy in hypophosphatasia," *Neuronal Tissue-Nonespecific Alkaline Phosphatase (TNAP): Subcellular Biochemistry*. Caroline Fonta and Laszlo Negyessy, 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914- 016-0309-0 (2016) (11 pages).
Mornet, "Hypophosphatasia," Metabolism. 82:142-155; DOI: 10.1016/j.metabol.2017.08.013 (2018) (30 pages).
Mornet, "Chapter 2: Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017) (1 page).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).

(56) References Cited

OTHER PUBLICATIONS

Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
De Roo et al., "Infantile hypophosphatasia without bone deformities presenting with severe pyridoxine-resistant seizures," Mol Genet Metab. 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of E. coli," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).

Park et al., "Ex vivo assessment of contractility, fatigability and alternans in isolated skeletal muscles," J Vis Exp. 69:e4198 (2012) (8 pages).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012) (1 page).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
National Institute for Health and Care Excellence, "Highly Specialised Technology Evaluation: Asfotase alfa for treating paediatric-onset hypophosphatasia [ID 758]," Oct. 21, 2015, <www.nice.org.uk/guidance/hst6/documents/committee-papers-8> (99 pages).
Tomazos et al., "Determination of the Minimal Clinically Important Difference in the Six-Minute Walk Test for Patients with Hypophosphatasia," 55th Annual European Society for Paediatric Endocrinology Meeting, September 10-12, Paris, France. 86, Abstract FC2.5, <abstracts.eurospe.org/hrp/0086/hrp0086FC2.5.htm> (2016) (4 pages).
International Search Report and Written Opinion for International Application No. PCT/US18/26868, dated Sep. 7, 2018 (30 pages).
International Preliminary Report on Patentability for International Patent Application No. PCT/US2016/049983, dated Sep. 11, 2018 (9 pages).
"Sequence 4," SCORE Search Results for U.S. Appl. No. 12/599,679, retrieved Nov. 17, 2018 (2 pages).
Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c. 1112C>T, p.T3711) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).

(56) References Cited

OTHER PUBLICATIONS

Boulet et al., "A population-based study of craniosynostosis in metropolitan Atlanta, 1989-2003," Am J Med Genet A. 146A(8):984-91 (2008).
Chan et al., "Endoscope-assisted versus open repair of craniosynostosis: a comparison of perioperative cost and risk," J Craniofac Surg. 24(1):170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3(Suppl 3):S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).

Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Milláan, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c. 1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).

(56) References Cited

OTHER PUBLICATIONS

Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, October 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Communication pursuant to Rule 164(2)(b) and Article 94(3) EPC for European Patent Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).
Extended European Search Report for European Application No. 15907550.6, dated Jun. 4, 2019 (7 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (6 pages).
Official Action for Russian Patent Application No. 2017123540, dated Jul. 8, 2019 (15 pages).
Di Rocco et al. "Craniosynostosis and hypophosphatasia," Arch Pediatr. 24(5S2):5S89-5S92 (2017).
Official Action and Translation for Japanese Application No. 2017-539393, dated Sep. 17, 2019 (14 pages).
Whyte et al. "Natural history of perinatal and infantile hypophosphatasia: a retrospective study," J Pediatr. 209:116-124.e4 (2019) (13 pages).
Leung et al. "Outcome of perinatal hypophosphatasia in Manitoba Mennonites: a retrospective cohort analysis," JIMD Rep. 11:73-78 (2013).
Taketani et al. Chapter 9: Hypophosphatasia. *Human Pathobiochemistry*. T. Oohashi et al. (eds.), 91-100 (2019).
Morrison et al. "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Whyte et al. "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Mornet, "The tissue nonspecific alkaline phosphatase gene mutations database," <www.sesep.uvsq.fr/03_hypo_mutations.php>, last updated Nov. 28, 2019 (14 pages).
Hancarova et al. "Hypophosphatasia due to uniparental disomy," Bone. 81:765-766 (2015).
Carden et al. "Tracheomalacia and tracheobronchomalacia in children and adults: an in-depth review," Chest. 127(3):984-1005 (2005).
Murgu et al. "Tracheobronchomalacia and excessive dynamic airway collapse," Respirology. 11(4):388-406 (2006).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Park et al. "The effect of alendronate loaded biphasic calcium phosphate scaffolds on bone regeneration in a rat tibial defect model," Int J Mol Sci. 16(11):26738-53 (2015) (17 pages).
Li et al. "Timing of the initiation of bisphosphonates after surgery for fracture healing: a systematic review and meta-analysis of randomized controlled trials," Osteoporos Int. 26(2):431-41 (2015) (11 pages).
International Search Report and Written Opinion for International Application No. PCT/US2019/045963, dated Jan. 30, 2020 (26 pages).
Search Report and Translation for Application No. 2018109368, dated Feb. 5, 2020 (4 pages).
Wang et al. "The effects of tissue-non-specific alkaline phosphatase gene therapy on craniosynostosis and craniofacial morphology in the $FGFR2^{C342Y/+}$ mouse model of Crouzon craniosynostosis," Orthod Craniofac Res. 18 Suppl. 1(01):196-206 (2015).
Abrams et al., "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Office Action for Japanese Application No. 2018-508754, dated Jun. 30, 2020 (11 pages).
Phillips et al., "Gait Assessment in Children with Childhood Hypophosphatasia: Impairments in Muscle Strength and Physical Function," The Endocrine Society's 97th Annual Meeting & Expo, Mar. 5-8, San Diego, CA. (2017) (2 pages).
Office Action for European Patent Application No. 16739617.5, dated May 11, 2020 (10 pages).
Rodionova et al., "Hypophosphatasia in Adults: Clinical Cases and Literature Review," Osteoporosis and Bone Diseases. 18(2):25-28 (2015) 10.14341/osteo2015225-28 (English language abstract).
Office Action for Russian Patent Application No. 2018137822, dated Jul. 24, 2020 (20 pages).

(56) References Cited

OTHER PUBLICATIONS

Bishop et al., "Life-threatening hypophosphatasia (HPP): Results of up to two years bone-targeted Enzyme Replacement Therapy (ERT) in infants and young children," Bone. 48:S82 (2011).
Little et al., "Lineage tracking of myogenic progenitors in surgical models of tibial bone repair," Bone. 48(2):S82 (2011).
Kim et al., "Comparison of phenylketonuria (PKU) patients' height, weight and body mass index (BMI) to the general population," Mol Genet Metab. 105:328-329.
Whyte et al., "Treatment of children with hypophosphatasia (HPP) with ENB-0040: radiographic and DXA outcomes after 6 months of therapy," Horm Res Paediatr. 76(Suppl 2):26 (2011).
Office Action for Japanese Patent Application No. 2018-515934, dated Jul. 28, 2020 (7 pages).
Sequencia—"Bone targeted alkaline phosphatase," UniParc, (Nov. 11, 2010), Database No. HI520929 (1 page).
Seefried et al., "Long-term Effectiveness of Asfotase Alfa Treatment in Adults with Pediatric-onset Hypophosphatasia in Routine Clinical Practice" 2020 American Society for Bone and Mineral Research Virtual Conference, Sep. 11-15, 2020.
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020).
Seefried et al., "Long-term Effectiveness of Asfotase Alfa Treatment in Adults with Pediatric-onset Hypophosphatasia in Routine Clinical Practice" 2020 World Congress of Osteoporosis, Osteoarthritis, and Muscoskeletal Diseases, Aug. 20-23, Barcelona, Spain (2020).
Anonymous: "Scale-up of CHO fed-batch cultures in HyClone (TM) ActiPro (TM) medium supplemented with Cell Boost (TM) 7a and 7b," Oct. 11, 2016, pp. 1-4, XP055461185.
Song et al., "Preliminary study on the effect of $Zn^{2+}$ on the activities of peptidase and alkaline phosphatase," Marine Sciences. 27(3):64-65 (2003) (Abstract only).
Office Action for Chinese Patent Application No. 201680048588.5, dated Jan. 18, 2021 (28 pages).
Dutta et al., "Men and mice: Relating their ages," Article in Press, published in final edited form as: Life Sci. 152:244-8 (2016) (5 pages).
Zhang et al., "Engineering E. coli Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).
"Data file 29-0929-25 AA. Xcellerex™ XDR cell culture bioreactor systems," GE Healthcare Life Sciences, published Feb. 2014 (4 pages).
Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Database Accession No. NM_000478.2, <https://www.ncbi.nlm.nih.gov/nuccore/NM_000478.2>, retrieved on Feb. 23, 2021 (7 pages).
Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).
Abbruzzese, "The Tinetti Performance-Oriented Mobility Assessment Tool," Am J Nursing. 98(12):16J-16L (1998) (3 pages).
International Search Report and Written Opinion for International Patent Application No. PCT/US20/64140, dated Apr. 23, 2021 (16 pages).
Kishnani et al., "Five-year efficacy and safety of asfotase alfa therapy for adults and adolescents with hypophosphatasia," Bone. 121:149-162 (2019).
Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, <https://www.clinicaltrials.gov/ct2/show/NCT00739505>, last updated Mar. 29, 2019 (8 pages).
Alexion Pharmaceuticals, "Safety and Efficacy Study of Asfotase Alfa in Adolescents and Adults With Hypophosphatasia (HPP)," ClinicalTrials.gov. NCT01163149, <https://clinicaltrials.gov/ct2/show/NCT01163149>, last updated Mar. 13, 2019 (9 pages).
Alexion Pharmaceuticals, "Strensiq™ (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCILMQAvD_BWE>, dated Nov. 5, 2015 (1 page).
European Medicines Agency, "Strensiq: Asfotase Alfa," <www.ema.europa.eu/en/medicines/human/EPAR/strensiq>, last updated Mar. 25, 2021 (8 pages).
Hofmann et al., "Efficacy and safety of asfotase alfa in infants and young children with hypophosphatasia: a phase 2 open-label study," J Clin Endocrinol Metab. 104(7): 2735-2747 (2019) (14 pages).
Examination Report No. 1 for Australian Patent Application No. 2016308624, dated Aug. 27, 2021 (6 pages).
Kim et al., "CHO cells in biotechnology for production of recombinant proteins: current state and further potential," Appl Microbiol Biotechnol. 93(3):917-30 (2012).
McCormack et al., "Is bigger better? An argument for very low starting doses," CMAJ. 183(1):65-9 (2011).
Rush, "Childhood hypophosphatasia: to treat or not to treat," Orphanet J Rare Dis. 13(1):116(2018) (5 pages).
Phillips et al., "Clinical Outcome Assessments: Use of Normative Data in a Pediatric Rare Disease," Value Health. 21(5):508-514 (2018).
Decision on Rejection for Chinese Patent Application No. 201680048588.5, dated Jan. 20, 2022 (19 pages).
Communication pursuant to Article 94(3) EPC for European Patent Application No. 16758322.8, dated Jan. 25, 2022 (3 pages).
Office Action for Japanese Patent Application No. 2019-548417, dated Jan. 18, 2022 (8 pages).
"Effects of feeding strategy on CHO cell performance in fed-batch cultures using HyClone ActiPro medium and Cell Boost 7a and 7b supplements," Cytiva, <http://www.processdevelopmentforum.com/posters/effects-of-feeding-strategy-on-cho-cell-performance-in-fed-batch-cultures/>. 2017 (5 pages).
Examination Report No. 2 for Australian Patent Application No. 2016308624, dated Apr. 7, 2022 (4 pages).
Witkowski et al., "Conversion of a beta-ketoacyl synthase to a malonyl decarboxylase by replacement of the active-site cysteine with glutamine," Biochemistry. 38(36):11643-50 (1999).
Whisstock et al., "Prediction of protein function from protein sequence and structure," Q Rev Biophys. 36(3):307-40 (2003).
Pharmaceutical and Food Safety Bureau Examination and Management Division / Pharmaceuticals and Medical Devices Agency, Review Report. 1-63 (2015) (English Abstract) (64 pages).
Office Action for Chinese Patent Application No. 201780021666.7, dated Jun. 20, 2022 (22 pages).
International Search Report and Written Opinion for International Patent Application No. PCT/US2022/025648, dated Jul. 22, 2022 (12 pages).
Notice of Final Rejection for Korean Patent Application No. 10-2018-7028255, dated Aug. 18, 2022 (7 pages).
Office Action for Brazilian Patent Application No. BR112018070243-9, dated Sep. 7, 2022 (10 pages).

(56) References Cited

OTHER PUBLICATIONS

International Search Report and Written Opinion of the International Searching Authority for International Application No. PCT/US2020/064140, dated Apr. 23, 2021 (12 pages).
GenBank NM_000478.2, "*Homo sapiens* alkaline phosphatase, liver/bone/kidney (ALPL), mRNA," <https://www.ncbi.nlm.nih.gov/nuccore/NM_000478.2>, dated Sep. 17, 2006, retrieved on Feb. 23, 2021 (7 pages).
International Search Report and Written Opinion for International Patent Application No. PCT/US2022/016031, dated May 3, 2022 (9 pages).
Office Action for Canadian Patent Application No. 2,993,358, dated Sep. 20, 2022 (6 pages).
An et al., "IgG2m4, an engineered antibody isotype with reduced Fc function," mAbs. 1(6): 572-579 (2009).
Komaru et al., "Molecular and cellular basis of hypophosphatasia," J Oral Biosci. 61(3):141-148 (Sep. 2019).
Sharma et al., "Alkaline Phosphatase: An Overview," Indian J Clin Biochem. 29(3):269-278 (2014).

\* cited by examiner

METHOD FOR PRODUCING RECOMBINANT ALKALINE PHOSPHATASE

FIELD OF THE DISCLOSURE

In general, this disclosure relates to methods of manufacturing recombinant polypeptides and recombinant glycoproteins i.e., alkaline phosphatase, in particular to methods of manufacturing recombinant fusion proteins, including but not limited to asfotase alfa.

There is a need in the art to develop effective therapeutic molecules and methods for treating diseases, particularly diseases having skeletal manifestations, such as hypophosphatasia. For recombinant polypeptides and recombinant glycoproteins, such as asfotase alfa, control of the physical parameters of the product is particularly important.

A method of producing recombinant alkaline phosphatase comprising: (a) inoculating Chinese Hamster Ovary (CHO) cells expressing recombinant alkaline phosphatase in culture medium, (b) culturing the CHO cells in culture medium, (c) adding nutrient supplements to the cell culture of (b) at least one day after inoculation, (d) isolating the recombinant alkaline phosphatase from the cell culture of (c) by at least one purification step to form harvest clarified culture fluid (HCCF) with a total sialic acid content (TSAC) of about 1.5 mol/mol to about 4.0 mol/mol, (e) performing at least one additional protein purification step to form a filtration pool (UFDF), wherein the UFDF is held at a temperature of from about 13° C. to about 27° C. for from about 1 hour to about 60 hours, and at a protein concentration of from about 1.7 g/L to about 5.3 g/L; and (f) subjecting the UFDF to at least one chromatography step to obtain partially purified recombinant alkaline phosphatase, wherein the recombinant alkaline phosphatase has a TSAC of about 0.9 mol/mol to about 3.0 mol/mol.

BACKGROUND

Hypophosphatasia (HPP) is a life-threatening, genetic, and ultra-rare metabolic disorder that results in a failure to produce functional tissue nonspecific alkaline phosphatase (TNSALP). It leads to the accumulation of unmineralized bone matrix (e.g. rickets, osteomalacia), characterized by hypo-mineralization of bones and teeth. When growing bone does not mineralize properly, impairment of growth disfigures joints and bones. This result in turn impacts motor performance, respiratory function, and may even lead to death. Different forms of HPP include perinatal, infantile, juvenile (or childhood), and adult HPP. Recently, six clinical forms have been defined, most based upon age at symptom onset, including perinatal, benign prenatal, infantile, juvenile, adult, and odonto-HPP. Asfotase alfa is an approved, first-in-class targeted enzyme replacement therapy designed to address defective endogenous TNSALP levels. For the first reports of treating HPP with TNSALP, see Whyte et al., 2012 *N Engl J Med*. 366:904-13.

Asfotase alfa (STRENSIQ®, Alexion Pharmaceuticals, Inc.) is a soluble fusion glycoprotein comprised of the catalytic domain of human TNSALP, a human immunoglobulin G1 Fc domain, and a deca-aspartate peptide (i.e., $D_{10}$) used as a bone-targeting domain. In vitro, asfotase alfa binds with a greater affinity to hydroxyapatite than does soluble TNSALP lacking the deca-aspartate peptide, thus allowing the TNSALP moiety of asfotase alfa to efficiently degrade excess local inorganic pyrophosphate (PPi) and restore normal mineralization to bones. Pyrophosphate hydrolysis promotes bone mineralization, and its effects were similar among the species evaluated in nonclinical studies.

Production of commercial scale quantities of therapeutically effective alkaline phosphatases (e.g., asfotase alfa) requires a complicated, sensitive, and multi-step process. The present disclosure provides for a method of manufacturing glycoproteins, including alkaline phosphatases such as asfotase alfa, with improved control of the final protein product characteristics.

BRIEF SUMMARY

Disclosed herein are improved manufacturing processes that can be used to increase efficiency in the production of alkaline phosphatases (e.g., asfotase alfa). Methods as described here can also be used for maintaining, preserving, modulating and/or improving the enzymatic activity of a recombinant protein, such as alkaline phosphatases (e.g., asfotase alfa) produced by cultured mammalian cells, particularly by cultured Chinese Hamster Ovary (CHO) cells. Such alkaline phosphatases (e.g., asfotase alfa) are suited for use in therapy, for example, for treatment of conditions associated with decreased alkaline phosphatase protein levels and/or function (e.g., insufficient cleavage of inorganic pyrophosphate (PPi), HPP, etc.) in a subject, for example, a human subject.

In one aspect, the present disclosure provides a method for producing a recombinant polypeptide having alkaline phosphatase function. In various embodiments, the alkaline phosphatase function may include any functions of alkaline phosphatase known in the art, such as enzymatic activity toward natural substrates including phosphoethanolamine (PEA), inorganic pyrophosphate (PPi) and pyridoxal 5'-phosphate (PLP). Such recombinant polypeptide can comprise asfotase alpha (SEQ ID NO: 1).

In some embodiments, the disclosure is directed to a method of producing recombinant alkaline phosphatase comprising: (a) inoculating Chinese Hamster Ovary (CHO) cells expressing recombinant alkaline phosphatase in culture medium; (b) culturing the CHO cells in culture medium; (c) isolating the recombinant alkaline phosphatase from the cell culture of (c) by at least one purification step to form harvest clarified culture fluid (HCCF) with a total sialic acid content (TSAC) of about 2.1 mol/mol to about 4.3 mol/mol; (d) performing at least one additional protein purification step to form a filtration pool (UFDF), wherein the UFDF is held at a temperature of from about 13° C. to about 27° C. for from about 1 hour to about 60 hours, and at a protein concentration of from about 1.7 g/L to about 5.3 g/L; and (e) subjecting the UFDF to at least one chromatography step to obtain partially purified recombinant alkaline phosphatase, wherein the recombinant alkaline phosphatase has a TSAC of about 0.7 mol/mol to about 3.5 mol/mol.

In some embodiments, the disclosure is directed to a method further comprising adding nutrient supplements to the cell culture of (b) after inoculation.

In some embodiments, the disclosure provides a method of producing recombinant alkaline phosphatase comprising: (a) inoculating Chinese Hamster Ovary (CHO) cells expressing recombinant alkaline phosphatase in culture medium; (b) culturing the CHO cells in culture medium; (c) adding nutrient supplements to the cell culture of (b) at least one day after inoculation; (d) isolating the recombinant alkaline phosphatase from the cell culture of (c) by at least one purification step to form a filtration pool; and (e) recovering the recombinant alkaline phosphatase from the filtration pool, wherein the recombinant alkaline phosphatase in the filtration pool has a total sialic acid content (TSAC) of from about 2.1 to about 4.3 mol/mol when subjected to the recovery.

In some embodiments, the recombinant alkaline phosphatase in the filtration pool has a TSAC of from about 2.2 mol/mol to about 3.6 mol/mol when subjected to the recovery. In some embodiments, the recombinant alkaline phosphatase in the filtration pool has a TSAC of from about 2.2 mol/mol to about 3.4 mol/mol when subjected to the recovery.

In some embodiments, the sialidase is selectively removed from the cell culture, the HCCF, and/or the UFDF. In some embodiments, an exogenous sialyltransferase is added to the cell culture, the HCCF, and/or the UFDF.

In some embodiments, the culturing of the CHO cells in the culture media is at a temperature of from about 36° C. to about 38° C. In some embodiments, the culturing of the CHO cells in the culture media is at a temperature of about 37° C. In some embodiments, the nutrient supplements are added to the cell culture at least one day after inoculation of CHO cells into the culture medium. In some embodiments, the nutrient supplements are added at more than 2 different times. In some embodiments, the culture medium is selected from the group consisting of EX-CELL® 302 Serum-Free Medium; CD DG44 Medium; BD Select™ Medium; SFM4CHO Medium; and combinations thereof.

In some embodiments, the culturing of the CHO cells is in a 0.25 L to 25,000 L bioreactor. In some embodiments, the culturing of the CHO cells is in a 100 L to 25,000 L bioreactor. In some embodiments, the culturing of the CHO cells is in a 2000 L to 20,000 L bioreactor. In some embodiments, the temperature of the cell culture is decreased from about 80 hours to about 120 hours after the inoculation. In some embodiments, step (d) occurs about 10 to about 14 days after inoculation.

In some embodiments, the TSAC of the HCCF is from about 2.2 mol/mol to about 3.6 mol/mol. In some embodiments, the TSAC of the HCCF is from about 2.2 mol/mol to about 3.4 mol/mol. In some embodiments, the one additional purification step comprises at least one of harvest clarification, filtration, ultrafiltration, diafiltration, viral inactivation, affinity capture, and combinations thereof. In some embodiments, the one additional purification step comprises ultrafiltration and/or diafiltration.

In some embodiments, the UFDF is held at a temperature of about 14° C. to about 26° C. In some embodiments, the UFDF is held at a temperature of about 15° C. to about 26° C. In some embodiments, the UFDF is held at a temperature of about 15° C. to about 25° C. In some embodiments, the UFDF is held at a temperature of about 19° C. to about 25° C.

In some embodiments, the UFDF is held for about 10 hours to about 50 hours. In some embodiments, the UFDF is held for about 12 hours to about 48 hours. In some embodiments, the UFDF is held for about 14 hours to about 42 hours. In some embodiments, the UFDF is held for about 17 hours to about 34 hours. In some embodiments, the UFDF is held for about 19 hours to about 33 hours. In some embodiments, the UFDF is held for about 25 hours to about 38 hours. In some embodiments, the UFDF is held for about 29 hours to about 35 hours.

In some embodiments, the UFDF has a protein concentration from about 2.0 g/L to about 4.3 g/L. In some embodiments, the UFDF has a protein concentration from about 2.4 g/L to about 3.7 g/L. In some embodiments, the UFDF has a protein concentration of about 3.1 g/L. In some embodiments, the UFDF has an alkaline phosphatase concentration from about 3.0 g/L to about 4.5 g/L. In some embodiments, the UFDF has an alkaline phosphatase concentration from about 3.3 g/L to about 4.1 g/L. In some embodiments, the alkaline phosphates is asfotase alfa.

In some embodiments, the at least one chromatography step is protein affinity chromatography. In some embodiments, the at least one chromatography step is Protein A chromatography. In some embodiments, step (d) further comprises a viral inactivation step. In some embodiments, step (e) further comprises at least one additional chromatography step and/or purification step.

In some embodiments, the at least one additional chromatography step comprises column chromatography. In some embodiments, the column chromatography comprises hydrophobic interaction chromatography. In some embodiments, the at least one additional purification step comprises an additional diafiltration. In some embodiments, the one additional chromatography and/or purification step comprises hydrophobic interaction chromatography and/or at least one additional diafiltration step. In some embodiments, the at least one additional chromatography step is performed to obtain recombinant alkaline phosphatase with a TSAC of about 0.9 mol/mol to about 3.9 mol/mol. In some embodiments, the at least one additional chromatography step is performed to obtain recombinant alkaline phosphatase with a TSAC of about 1.1 mol/mol to about 3.2 mol/mol. In some embodiments, the at least one additional chromatography step is performed to obtain recombinant alkaline phosphatase with a TSAC of about 1.4 mol/mol to about 3.0 mol/mol. In some embodiments, the at least one additional chromatography step is performed to obtain recombinant alkaline phosphatase with a TSAC of about 1.2 mol/mol to about 3.0 mol/mol.

In some embodiments, the recombinant alkaline phosphatase comprises the structure of W-sALP-X-Fc-Y-$D_n$-Z, wherein (i) W is absent or is an amino acid sequence of at least one amino acid; (ii) X is absent or is an amino acid sequence of at least one amino acid; (iii) Y is absent or is an amino acid sequence of at least one amino acid; (iv) Z is absent or is an amino acid sequence of at least one amino acid; (v) Fc is a fragment crystallizable region; (vi) $D_n$ is a poly-aspartate, poly-glutamate, or combination thereof, wherein n=10 or 16; and (vii) sALP is a soluble alkaline phosphatase. In some embodiments, the recombinant alkaline phosphatase comprises asfotase alfa (SEQ ID NO: 1).

In some embodiments, the recombinant alkaline phosphatase obtained from the protein affinity chromatography is stored at from about 2° C. to about 8° C.

In some embodiments, the disclosure provides a method additionally comprising measuring recombinant alkaline phosphatase activity.

In some embodiments, the disclosure provides a recombinant alkaline phosphatase produced in a mammalian cell culture, wherein the recombinant alkaline phosphatase in a filtration pool produced from the cell culture has a total sialic acid content (TSAC) greater than or equal to about 1.2 mol/mol, and wherein the mammalian cell culture is about 100 L to about 25,000 L.

In some embodiments, the disclosure provides a filtration pool (UFDF) comprising recombinant alkaline phosphatase, wherein the UFDF is produced from about 100 L to about 25,000 L cell culture, and wherein the UFDF is held at from about 19° C. to about 25° C., for from about 14 to about 42 hours, at a protein concentration of from about 2.0 to about 4.3 g/L.

In some embodiments, the disclosure provides a recombinant alkaline phosphatase produced by the methods as described herein.

In some embodiments, the disclosure provides a pharmaceutical formulation comprising a recombinant alkaline phosphatase produced by a method as described herein, and at least one pharmaceutically acceptable carrier, diluent, excipient, or combination thereof.

In some embodiments, the disclosure provides a method of using the recombinant alkaline phosphatase made by the methods described herein to increase cleavage of inorganic pyrophosphate (PPi) in a subject.

In some embodiments, the disclosure is directed to a method of treating a subject suffering from a condition associated with alkaline phosphatase deficiency, comprising administering to the subject a therapeutically effective amount of the recombinant alkaline phosphatase produced by the methods described herein.

In some embodiments, the disclosure is directed to a method of controlling total sialic acid content (TSAC) in a TSAC-containing recombinant protein through mammalian cell culturing, comprising at least one purification step and at least one chromatography step.

In some embodiments, the disclosure is directed to a method of controlling glycosidase activity in mammalian cell culture producing a recombinant protein, comprising at least one purification step and at least one chromatography step.

In some embodiments, the recombinant protein is a recombinant enzyme. In some embodiments, the recombinant protein is an alkaline phosphatase protein. In some embodiments, the recombinant protein is asfotase alfa. In some embodiments, the glycosidase is sialidase. In some embodiments, the at least one purification step comprises ultrafiltration and/or diafiltration, and the at least one chromatography step comprises protein A chromatography.

BRIEF DESCRIPTION OF THE DRAWINGS

In the appended drawings:

FIG. 3A suggests an increase in TSAC decline rate by 0.11 mol/mol/10 hr every 1 g/L increase in UF1 concentration (Location 1 (LNH): mean: 2.1 g/L and Location 2 (LBH): mean: 3.3 g/L). FIG. 3B suggests an increase in TSAC decline rate by 0.11 mol/mol/10 hr for every 1° C. increase in UF1 hold temperature.

DETAILED DESCRIPTION

Definitions

Figure 1:
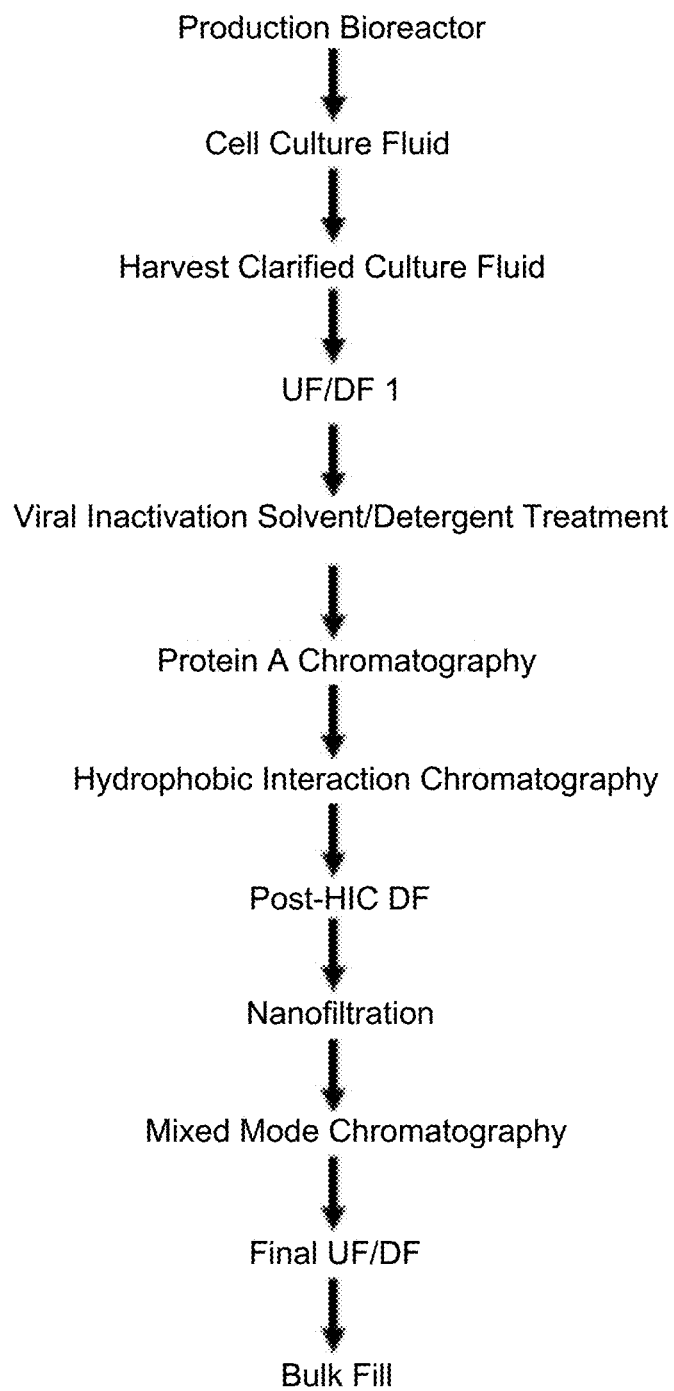
FIG. 1 illustrates an embodiment of the methods described herein for production of asfotase alfa.

"About", "Approximately": As used herein, the terms "about" and "approximately", as applied to one or more particular cell culture conditions or numerical values, refer to a range of values that are similar to the stated reference value for that culture condition, conditions, or numerical values. In certain embodiments, the term "about" refers to a range of values that fall within 25, 20, 19, 18, 17, 16, 15, 14, 13, 12, 11, 10, 9, 8, 7, 6, 5, 4, 3, 2, or 1 percent or less of the stated reference value for that culture condition, conditions, or numerical values.

"Amino acid": The term "amino acid," as used herein, refers to any of the twenty naturally occurring amino acids that are normally used in the formation of polypeptides, or analogs or derivatives of those amino acids Amino acids of the present disclosure can be provided in medium to cell cultures. The amino acids provided in the medium may be provided as salts or in hydrate form.

"Batch culture": The term "batch culture," as used herein, refers to a method of culturing cells in which all of the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified. In some embodiments, the methods described here are used in a batch culture.

"Bioreactor": The term "bioreactor" as used herein refers to any vessel used for the growth of a cell culture (e.g., a mammalian cell culture). The bioreactor can be of any size so long as it is useful for the culturing of cells. Typically, the bioreactor will be at least 1 liter and may be 10, 100, 250, 500, 1000, 2500, 5000, 8000, 10,000, 12,0000, 20,000 liters or more, or any volume in between. In some embodiments, the bioreactor is 100 liters to 25,000 liters, 500 liters to 20,000 liters, 1,000 liters to 20,000 liters, 2,000 liters to 20,000 liters, 5,000 liters to 20,000 liters, or 10,000 liters to 20,000 liters. The internal conditions of the bioreactor, including, but not limited to pH and temperature, are typically controlled during the culturing period. The bioreactor can be composed of any material that is suitable for holding mammalian or other cell cultures suspended in media under the culture conditions of the present disclosure, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2500, 5000, 8000, 10,000, 12,0000, 20,000 liters or more, or any volume in between. One of ordinary skill in the art will be aware of and will be able to choose suitable bioreactors for use in practicing the present disclosure.

"Cell density": The term "cell density," as used herein, refers to the number of cells present in a given volume of medium.

"Cell viability": The term "cell viability," as used herein, refers to the ability of cells in culture to survive under a given set of culture conditions or experimental variations. The term as used herein also refers to that portion of cells which are alive at a particular time in relation to the total number of cells, living and dead, in the culture at that time.

"Culture" and "cell culture": These terms, as used herein, refer to a cell population that is suspended in a medium (see definition of "medium" below) under conditions suitable for survival and/or growth of the cell population. As will be clear to those of ordinary skill in the art, these terms as used herein may refer to the combination comprising the cell population and the medium in which the population is suspended.

"Fed-batch culture": The term "fed-batch culture," as used herein, refers to a method of culturing cells in which additional components are provided to the culture at some time subsequent to the beginning of the culture process. The provided components typically comprise nutritional supplements for the cells, which have been depleted during the culturing process. A fed-batch culture is typically stopped at some point and the cells and/or components in the medium are harvested and optionally purified. Fed-batch culture may be performed in the corresponding fed-batch bioreactor. In some embodiments, the method comprises a fed-batch culture.

"Fragment": The term "fragment," as used herein, refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In some embodiments the fraction of activity retained is at least 10% of the activity of the full-length polypeptide. In various embodiments the fraction of activity retained is at least 20%, 30%, 40%, 50%, 60%, 70%, 80%, or 90% of the activity of the full-length polypeptide. In other embodiments the fraction of activity retained is at least 95%, 96%, 97%, 98%, or 99% of the activity of the full-length polypeptide. In one embodiment, the fraction of activity retained is 100% of the activity of the full-length polypeptide. The term as used herein also refers to any portion of a given polypeptide that includes at least an established sequence element found in the full-length polypeptide. In some embodiments, the sequence element spans at least 4-5 amino acids of the full-length polypeptide. In some embodiments, the sequence element spans at least about 10, 15, 20, 25, 30, 35, 40, 45, 50 or more amino acids of the full-length polypeptide.

"Glycoprotein" or "glycoproteins: These terms, as used herein, refer to a protein or polypeptide with carbohydrate groups (such as sialic acid) attached to the polypeptide chain.

"Medium", "media", "cell culture medium", and "culture medium": These terms, as used herein, refer to a solution containing nutrients which nourish growing mammalian cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is, e.g., formulated to a pH and salt concentration optimal for cell survival and proliferation. In some embodiments, a culture medium may be a "defined media"—a serum-free media that contains no proteins, hydrolysates or components of unknown composition. Defined media are free of animal-derived components and all components have a known chemical structure. In some embodiments, the culture medium is a basal medium, i.e., an undefined medium containing a carbon source, water, salts, a source of amino acids and nitrogen (e.g., animal, e.g., beef, or yeast extracts). Various mediums are commercially available and are known to those in the art. In some embodiments, the culture medium is selected from EX-CELL® 302 Serum-Free Medium (Signam Aldrich, St. Louis, MO), CD DG44 Medium (ThermoFisher Scientific, Waltham, MA), BD Select Medium (BD Biosciences, San Jose, CA), or a mixture thereof. a mixture of BD Select Medium with SFM4CHO Medium (Hyclone, Logan UT). In some embodiments, the culture medium comprises a combination of SFM4CHO Medium and BD Select™ Medium. In some embodiments, the culture medium comprises a combination of SFM4CHO Medium and BD Select™ Medium at a ratio selected from 90/10, 80/20, 75/25, 70/30, 60/40, or 50/50. In some embodiments, the culture medium comprises a combination of SFM4CHO Medium and BD Select™ Medium at a ratio of 70/30 to 90/10. In some embodiments, the culture medium comprises a combination of SFM4CHO Medium and BD Select™ Medium at a ratio 75/25.

"Osmolality" and "osmolarity": Osmolality is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of solution (1 mOsm/kg $H_2O$ at 38° C. is equivalent to an osmotic pressure of 19 mm Hg). "Osmolarity," by contrast, refers to the number of solute particles dissolved in 1 liter of solution. When used herein the abbreviation "mOsm" means "milliosmoles/kg solution".

"Perfusion culture": The term "perfusion culture," as used herein, refers to a method of culturing cells in which additional components are provided continuously or semi-continuously to the culture subsequent to the beginning of the culture process. The provided components typically comprise nutritional supplements for the cells, which have been depleted during the culturing process. A portion of the cells and/or components in the medium are typically harvested on a continuous or semi-continuous basis and are optionally purified. In some embodiments, the nutritional supplements as described herein are added in a perfusion culture, i.e., they are provided continuously over a defined period of time.

"Polypeptide": The term "polypeptide," as used herein, refers a sequential chain of amino acids linked together via peptide bonds. The term is used to refer to an amino acid chain of any length, but one of ordinary skill in the art will understand that the term is not limited to lengthy chains and can refer to a minimal length chain comprising two amino acids linked together via a peptide bond.

"Protein": The term "protein," as used herein, refers to one or more polypeptides that function as a discrete unit. If a single polypeptide is the discrete functioning unit and does not require permanent physical association with other polypeptides in order to form the discrete functioning unit, the terms "polypeptide" and "protein" as used herein are used interchangeably.

"Recombinantly-expressed polypeptide" and "recombinant polypeptide": These terms, as used herein, refer to a polypeptide expressed from a host cell that has been genetically engineered to express that polypeptide. The recombinantly-expressed polypeptide can be identical or similar to a polypeptide that is normally expressed in the mammalian host cell. The recombinantly-expressed polypeptide can also be foreign to the host cell, i.e., heterologous to peptides normally expressed in the host cell. Alternatively, the recombinantly-expressed polypeptide can be chimeric in that portions of the polypeptide contain amino acid sequences that are identical or similar to polypeptides normally expressed in the mammalian host cell, while other portions are foreign to the host cell.

"Seeding": The term "seeding," as used herein, refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell. In various embodiments, alkaline phosphatase (e.g., asfotase alfa) is produced by a process in which cells are seeded in a density of about $1.0 \times 10^5$ cells/mL, $1.5 \times 10^5$ cells/mL, $2.0 \times 10^5$ cells/mL, $2.5 \times 10^5$ cells/mL, $3.0 \times 10^5$ cells/mL, $3.5 \times 10^5$ cells/mL, $4.0 \times 10^5$ cells/mL, $4.5 \times 10^5$ cells/mL, $5.0 \times 10^5$ cells/mL, $5.5 \times 10^5$ cells/mL, $6.0 \times 10^5$ cells/mL, $6.5 \times 10^5$ cells/mL, $7.0 \times 10^5$ cells/mL, $7.5 \times 10^5$ cells/mL, $8.0 \times 10^5$ cells/mL, $8.5 \times 10^5$ cells/mL, $9.0 \times 10^5$ cells/mL, $9.5 \times 10^5$ cells/mL, $1.0 \times 10^6$ cells/mL, $1.5 \times 10^6$ cells/mL, $2.0 \times 10^6$ cells/mL, or a higher density. In one particular embodiment, in such process cells are seeded in a density of about $4.0 \times 10^5$ cells/mL, $5.5 \times 10^5$ cells/mL or $8.0 \times 10^5$ cells/mL.

"Total Sialic Acid Content" or "TSAC": The term as used herein refers to the amount of sialic acid (a carbohydrate) on a particular protein molecule. It is expressed as moles TSAC per mole of protein, or, "mol/mol." TSAC concentration is measured during the purification process. For example, one method of TSAC quantitiation is where TSAC is released from asfotase alfa using acid hydrolysis, and the released TSAC is subsequently detected via electrochemical detection using high-performance anion-exchange chromatography with pulsed amperometric detection technique ("HPAE-PAD").

"Titer": The term "titer," as used herein, refers to the total amount of recombinantly-expressed polypeptide or protein produced by a cell culture divided by a given amount of medium volume. Titer is typically expressed in units of milligrams of polypeptide or protein per milliliter of medium.

Acronyms used herein include, e.g., HCCF: Harvest Clarified Culture Fluid; UF: ultrafiltration, DF: diafiltration; VCD: Viable Cell Density; IVCC: Integral of Viable Cell Concentration; TSAC: Total Sialic Acid Content; HPAE-PAD: High-Performance Anion Exchange Chromatography with Pulsed Amperometric Detection; SEC: Size Exclusion Chromatography; AEX: Anion Exchange Chromatography; LoC: Lab-on-Chip; and MALDI-TOF: Matrix Assisted Laser Desorption/Ionization—Time of Flight.

As used herein, the term "hydrophobic interaction chromatography (HIC) column" refers to a column containing a stationary phase or resin and a mobile or solution phase in which the hydrophobic interaction between a protein and hydrophobic groups on the stationary phase or resin separates a protein from impurities including fragments and aggregates of the subject protein, other proteins or protein fragments and other contaminants such as cell debris, or residual impurities from other purification steps. The stationary phase or resin comprises a base matrix or support such as a cross-linked agarose, silica or synthetic copolymer material to which hydrophobic ligands are attached. Examples of such stationary phase or resins include phenyl-, butyl-, octyl-, hexyl- and other alkyl substituted agarose, silica, or other synthetic polymers. Columns may be of any size containing the stationary phase, or may be open and batch processed. In some embodiments, the recombinant alkaline phosphatase is isolated from the cell culture using HIC.

As used herein, the term "preparation" refers to a solution comprising a protein of interest (e.g., a recombinant alkaline phosphatase described herein) and at least one impurity from a cell culture producing such protein of interest and/or a solution used to extract, concentrate, and/or purify such protein of interest from the cell culture. For example, a preparation of a protein of interest (e.g., a recombinant alkaline phosphatase described herein) may be prepared by homogenizing cells, which grow in a cell culture and produce such protein of interest, in a homogenizing solution. In some embodiments, the preparation is then subjected to one or more purification/isolation process, e.g., a chromatography step.

As used herein, the term "solution" refers to a homogeneous, molecular mixture of two or more substances in a liquid form. Specifically, in some embodiments, the proteins to be purified, such as the recombinant alkaline phosphatases or their fusion proteins (e.g., asfotase alfa) in the present disclosure represent one substance in a solution. The term "buffer" or "buffered solution" refers to solutions which resist changes in pH by the action of its conjugate acid-base range. Examples of buffers that control pH at ranges of about pH 5 to about pH 7 include HEPES, citrate, phosphate, and acetate, and other mineral acid or organic acid buffers, and combinations of these. Salt cations include sodium, ammonium, and potassium. As used herein the term "loading buffer/solution" or "equilibrium buffer/solution" refers to the buffer/solution containing the salt or salts which is mixed with the protein preparation for loading the protein preparation onto a chromatography column, e.g., HIC column. This buffer/solution is also used to equilibrate the column before loading, and to wash to column after loading the protein. The "elution buffer/solution" refers to the buffer/solution used to elute the protein from the column. As used herein, the term "solution" refers to either a buffered or a non-buffered solution, including water.

The term "sialic acid" refers generally to N- or O-substituted derivatives of neuraminic acid, a monosaccharide with a nine-carbon backbone. Sialic acid may also refer specifically to the compound N-acetylneuraminic acid and is sometimes abbreviated as NeuSAc or NANA. Presence of sialic acid may affect absorption, serum half-life, and clearance of glycoproteins from the serum, as well as physical, chemical, and immunogenic properties of the glycoprotein. In some embodiments of the present disclosure, sialic acid associated with alkaline phosphatases, e.g., asfotase alfa, impacts the half-life of the molecule in physiological conditions. In some embodiments, precise and predictable control of total sialic acid content (TSAC) of asfotase alfa serves as a critical quality attribute for recombinant asoftase alfa. In some embodiments, the TSAC is 1.2 to 3.0 mol/mol asfotase alfa monomer. In some embodiments, TSAC is generated in the recombinant protein production process in the bioreactor. In some embodiments, the disclosure provides a method of controlling total sialic acid content (TSAC) in a TSAC-containing recombinant protein through mammalian cell culture, comprising at least one purification step and at least one chromatography step. In some embodiments, the purification and chromatography steps lead to decreased glycosidase activity, and thus increased total sialic acid content of the recombinant protein.

The term "sialylation" refers to a specific type of glycosylation, i.e., the addition of one or more sialic acid molecules to biomolecules, particularly, the addition of one or more sialic acid molecules to proteins. In some embodiments of the present disclosure, sialylation is performed by a sialyltransferase enzyme. In some embodiments, sialyltransferases add sialic acid to nascent oligosaccharides and/or to N- or O-linked sugar chains of glycoproteins. In some embodiments, sialyltransferases are present natively in the cells producing recombinant alkaline phosphatase. In some embodiments, sialyltransferases are present in the cell culture medium and/or nutrient supplement used in culturing the cells producing recombinant alkaline phosphatase. In some embodiments, sialyltransferases are produced recombinantly, using recombinant protein expression methods known in the art. In some embodiments, recombinant sialyltransferases produced separately from the recombinant alkaline phosphatases are added exogenously to the cell culture, the harvest clarified culture fluid (HCCF), and/or the filtration pool.

In some embodiments of the present disclosure, sialic acid groups are removed from glycoproteins (i.e., "desialylation") by hydrolysis. In some embodiments, desialylation is performed by a glycosidase enzyme. As used herein, "glycosidase," also called "glycoside hydrolase," is an enzyme that catalyzes the hydrolysis of a bond joining a sugar of a glycoside to an alcohol or another sugar unit. Examples of glycosidases include amylase, xylanase, cellulase, and sialidase. In some embodiments, desialylation is performed by a sialidase enzyme. In some embodiments, sialidases hydrolyze glycosidic linkages of terminal sialic acid residues in glycoproteins, glycolipids, oligosaccharides, colominic acid, and/or synthetic substrates. In some embodiments, sialidases are present in the cell culture medium producing recombinant alkaline phosphatase. In some embodiments, sialidase activity is dependent on and/or correlates with total protein concentration. In some embodiments, sialidases are essentially inactive until a critically high protein concentration, at which point the sialidase is activated. In some embodiments, sialidases are present in the HCCF or the filtration pool of the cell culture producing recombinant alkaline phosphatase. In some embodiments, sialidases remove sialic acid moieties from glycosylation sites on recombinant alkaline phosphatase, e.g., asfotase alfa, effectively reducing the TSAC of the recombinant alkaline phosphatase. In some embodiments, sialidases are selectively removed from the cell culture, the HCCF, and/or the filtration pool. Sialidases can be selectively removed by, e.g., one or a combination of sialidase-specific inhibitors, antibodies, ion exchange and/or affinity chromatography, immunoprecipitation, and the like. For an overview of how bioprocess conditions affect the sialic acid content of proteins, see Gramer et al., *Biotechnol. Prog.* 9(4):366-373 (1993), the disclosure of which is hereby incorporated by reference in its entirety. In some embodiments, the present disclosure provides a method of controlling glycosidase activity in mammalian cell culture producing recombinant protein, comprising at least one purification and at least one chromatography step. In some embodiments, the purification and chromatography steps lead to decreased glycosidase activity, and thus increased total sialic acid content of the recombinant protein.

The term "harvest clarified culture fluid," abbreviated as HCCF, refers to a clarified, filtered fluid harvested from a cell culture, e.g., a cell culture in a bioreactor. The HCCF is typically free of cells and cellular debris (such as, e.g., insoluble biomolecules) which may be present in the cell culture. In some embodiments of the present disclosure, HCCF is generated through centrifugation, depth filtration, sterile filtration, and/or chromatography. In some embodiments, a cell culture fluid from the bioreactor is first centrifuged and/or filtered, then subjected to at least one chromatography step in order to generate the HCCF. In some embodiments, the HCCF is concentrated prior to and/or after the at least one chromatography step. In some embodiments, the HCCF is diluted after the at least one chromatography step. In some embodiments, the HCCF from the cell culture producing recombinant alkaline phosphatase contains the recombinant alkaline phosphatase and contaminant proteins. In some embodiments, the contaminant proteins in the HCCF include sialidase enzymes.

The terms "filtration" and "flow filtration" refer to a pressure driven process that uses membranes to separate components in a liquid solution or suspension based on their size and charge differences. Flow filtration may be normal flow filtration or "tangential flow filtration," also known as TFF or cross-flow filtration. TFF is typically used for clarifying, concentrating, and purifying proteins. During a TFF process, fluid is pumped tangentially along the surface of at least one membrane. An applied pressure serves to force a portion of the fluid through the membrane to the downstream side as "filtrate." Particulates and macromolecules that are too large to pass through the membrane pores are retained on the upstream side as "retentate." TFF may be used in various forms, including, for example, microfiltration, ultrafiltration—which includes virus filtration and high performance TFF, reverse osmosis, nanofiltration, and diafiltration. In some embodiments of the present disclosure, one or more of the TFF forms are used in combination for protein processing and/or purification. In some embodiments, ultrafiltration and diafiltration are used in combination for purifying a recombinant alkaline phosphatase. Ultrafiltration and diafiltration are described herein.

"Ultrafiltration," or "UF," is a purification process used to separate proteins from buffer components for buffer exchange, desalting, or concentration. Depending on the protein to be retained, membrane molecular weight limits in the range of about 1 kD to about 1000 kD are used. In some embodiments, UF is a TFF process.

"Diafiltration," or "DF," is a purification process that washes smaller molecules through a membrane and leaves larger molecules in the retentate without ultimately changing concentration. Typically, DF is used in combination with another purification processes to enhance product yield and/or purity. During DF, solution (e.g., water or buffer) is introduced into the sample reservoir while filtrate is removed from the unit operation. In processes where the desired product is in the retentate, diafiltration washes components out of the product pool into the filtrate, thereby exchanging buffers and reducing the concentration of undesirable species. When the product is in the filtrate, diafiltration washes it through the membrane into a collection vessel. In some embodiments, DF is a TFF process.

The term "filtration pool," sometimes also referred to as the "UFDF pool" or the "UFDF," refers to a total volume of fluid from a filtration process, typically from a combined ultrafiltration/diafiltration (UF/DF) process. In the context of protein purification, the UFDF refers to the retentate from an ultrafiltration/diafiltration process.

The present disclosure provides a method of improving the yield, enzymatic function and consistency of a recombinant protein which is expressed by cell culture (e.g., mammalian cells including but not limited to Chinese Hamster Ovary (CHO) cells). Specifically, a recombinant protein may be produced by a certain type of cells (e.g., mammalian cells including but not limited to Chinese Hamster Ovary (CHO) cells) through, for example, a fermentation process. The total processes of inoculation and growth of the cells, induction of protein expression, and various parameter optimizations for protein expression are referred as upstream processing steps. Correspondingly, the downstream processing steps may include, e.g., the recovery and purification of the produced proteins (i.e., separation of the produced proteins from other impurities and/or contaminants originated from the cells and the culture medium). Exemplary downstream process steps include, for example, protein capturing from harvest, removing host cell debris, host cell proteins (HCPs), and host cell DNAs, endotoxins, viruses and other containments, buffer-exchanging, and formulation adjustment, etc.

The present disclosure provides a method of improving the yield, enzymatic function and consistency of an alkaline phosphatase (e.g., asfotase alfa) which is produced by cell culture.

The present disclosure provides a method of culturing cells (e.g., mammalian cells including but not limited to Chinese Hamster Ovary (CHO) cells) expressing a recombinant protein. The present disclosure provides manufacturing systems for the production of an alkaline phosphatase (e.g., asfotase alfa) by cell culture. In certain embodiments, systems are provided that minimize production of one or more metabolic products that are detrimental to cell growth, viability, and/or protein production or quality. In particular embodiments, the cell culture is a batch culture, a fed-batch culture, a culture or a continuous culture.

Alkaline Phosphtases (ALPS)

The present disclosure relates to the manufacturing of an alkaline phosphatase protein (e.g., asfotase alfa) in recombinant cell culture. The alkaline phosphatase protein includes any polypeptides or molecules comprising polypeptides that comprise at least some alkaline phosphatase activity. In various embodiments, the alkaline phosphatase disclosed herein includes any polypeptide having alkaline phosphatase functions, which may include any functions of alkaline phosphatase known in the art, such as enzymatic activity toward natural substrates including phosphoethanolamine (PEA), inorganic pyrophosphate (PPi) and pyridoxal 5'-phosphate (PLP).

In certain embodiments, such alkaline phosphatase protein, after being produced and then purified by the methods disclosed herein, can be used to treat or prevent alkaline phosphatase-related diseases or disorders. For example, such alkaline phosphatase protein may be administered to a subject having decreased and/or malfunctioned endogenous alkaline phosphatase, or having overexpressed (e.g., above normal level) alkaline phosphatase substrates. In some embodiments, the alkaline phosphatase protein in this disclosure is a recombinant protein. In some embodiments, the alkaline phosphatase protein is a fusion protein. In some embodiments, the alkaline phosphatase protein in this disclosure specifically targets a cell type, tissue (e.g., connective, muscle, nervous, or epithelial tissues), or organ (e.g., liver, heart, kidney, muscles, bones, cartilage, ligaments, tendons, etc.). For example, such alkaline phosphatase protein may comprise a full-length alkaline phosphatase (ALP) or fragment of at least one alkaline phosphatase (ALP). In some embodiments, the alkaline phosphatase protein comprises a soluble ALP (sALP) linked to a bone-targeting moiety (e.g., a negatively-charged peptide as described below). In some embodiments, the alkaline phosphatase protein comprises a soluble ALP (sALP) linked to an immunoglobulin moiety (full-length or fragment). For example, such immunoglobulin moiety may comprise a fragment crystallizable region (Fc). In some embodiments, the alkaline phosphatase protein comprises a soluble ALP (sALP) linked to both a bone-targeting moiety and an immunoglobulin moiety (full-length or fragment). For more detailed description of the alkaline phosphatase protein disclosed herein, see PCT Publication Nos. WO 2005/103263 and WO 2008/138131, the teachings of both of which are incorporated by reference herein in their entirety.

In some embodiments, the alkaline phosphatase protein described herein comprises any one of the structures selected from the group consisting of: sALP-X, X-sALP, sALP-Y, Y-sALP, sALP-X-Y, sALP-Y-X, X-sALP-Y, X-Y-sALP, Y-sALP-X, and Y-X-sALP, wherein X comprises a bone-targeting moiety, as described herein, and Y comprises an immunoglobulin moiety, as described herein. In one embodiment, the alkaline phosphatase protein comprises the structure of W-sALP-X-Fc-Y-$D_n/E_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n/E_n$ is a polyaspartate, polyglutamate, or combination thereof wherein n=8-20; and sALP is a soluble alkaline phosphatase (ALP). In some embodiments, $D_n/E_n$ is a polyaspartate sequence. For example, $D_n$ may be a polyaspartate sequence wherein n is any number between 8 and 20 (both included) (e.g., n may be 8, 9, 10, 11, 12, 13, 14, 15, 16, 17, 18, 19, and 20). In one embodiment, $D_n$ is $D_{10}$ or $D_{16}$. In some embodiments, $D_n/E_n$ is a polyglutamate sequence. For example, $E_n$ may be a polyglutamate sequence wherein n is any number between 8 and 20 (both included) (e.g., n may be 8, 9, 10, 11, 12, 13, 14, 15, 16, 17, 18, 19, or 20). In one embodiment, $E_n$ is $E_{10}$ or $E_{16}$.

For example, such sALPs may be fused to the full-length or fragment (e.g., the fragment crystallizable region (Fc)) of an immunoglobulin molecule. In some embodiments, the recombinant polypeptide comprises a structure of W-sALP-X-Fc-Y-$D_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n$ is a poly-aspartate, poly-glutamate, or combination thereof, wherein n=10 or 16; and said sALP is a soluble alkaline phosphatase. In one embodiment, n=10. In another embodiment, W and Z are absent from said polypeptide. In some embodiments, said Fc comprises a CH2 domain, a CH3 domain and a hinge region. In some embodiments, said Fc is a constant domain of an immunoglobulin selected from the group consisting of IgG-1, IgG-2, IgG-3, IgG-3 and IgG-4. In one embodiment, said Fc is a constant domain of an immunoglobulin IgG-1. In one particular embodiment, said Fc comprises the sequence as set forth in D488-K714 of SEQ ID NO: 1.

In some embodiments, the alkaline phosphatase disclosed herein comprises the structure of W-sALP-X-Fc-Y-$D_n$-Z, wherein W is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; Fc is a fragment crystallizable region; $D_n$ is a poly-aspartate, poly-glutamate, or combination thereof, wherein n=10 or 16; and said sALP is a soluble alkaline phosphatase. Such sALP is capable of catalyzing the cleavage of at least one of phosphoethanolamine (PEA), inorganic pyrophosphate (PPi) and pyridoxal 5'-phosphate (PLP). In various embodiments, the sALP disclosed herein is capable of catalyzing the cleavage of inorganic pyrophosphate (PPi). Such sALP may comprise all amino acids of the active anchored form of alkaline phosphatase (ALP) without C-terminal glycolipid anchor (GPI). Such ALP may be at least one of tissue-non-specific alkaline phosphatase (TNALP), placental alkaline phosphatase (PALP), germ cell alkaline phosphatase (GCALP), and intestinal alkaline phosphatase (IAP), or their chimeric or fusion forms or variants disclosed herein. In one particular embodiment, the ALP comprises tissue-non-specific alkaline phosphatase (TNALP). In another embodiment, the sALP disclosed herein is encoded by a polynucleotide encoding a polypeptide comprising the sequence as set forth in L1-S485 of SEQ ID NO: 1. In yet another embodiment, the sALP disclosed herein comprises the sequence as set forth in L1-S485 of SEQ ID NO: 1.

In one embodiment, the alkaline phosphatase protein comprises the structure of TNALP-Fc-$D_{10}$ (SEQ ID NO: 1, as listed below). Underlined asparagine (N) residues correspond to potential glycosylation sites (i.e., N 123, 213, 254, 286, 413 & 564). Bold underlined amino acid residues ($L_{486}$-$K_{487}$ & $D_{715}$-$I_{716}$) correspond to linkers between sALP and Fc, and Fc and $D_{10}$ domains, respectively.

```
                                               (SEQ ID NO: 1)
        10         20         30         40
LVPEKEKDPK YWRDQAQETL KYALELQKLN TNVAKNVIMF 50         60         70         80
LGDGMGVSTV TAARILKGQL HHNPGEETRL EMDKFPFVAL 90        100        110        120
SKTYNTNAQV PDSAGTATAY LCGVKANEGT VGVSAATERS 130        140        150        160
RCNTTQGNEV TSILRWAKDA GKSVGIVTTT RVNHATPSAA 170        180        190        200
YAHSADRDWY SDNEMPPEAL SQGCKDIAYQ LMHNIRDIDV 210        220        230        240
IMGGGRKYMY PKNKTDVEYE SDEKARGTRL DGLDLVDTWK 250        260        270        280
SFKPRYKHSH FIWNRTELLT LDPHNVDYLL GLFEPGDMQY 290        300        310        320
ELNRNNVTDP SLSEMVVVAI QILRKNPKGF FLLVEGGRID 330        340        350        360
HGHHEGKAKQ ALHEAVEMDR AIGQAGSLTS SEDTLTVVTA 370        380        390        400
DHSHVFTFGG YTPRGNSIFG LAPMLSDTDK KPFTAILYGN 410        420        430        440
GPGYKVVGGE RENVSMVDYA HNNYQAQSAV PLRHETHGGE 450        460        470        480
DVAVFSKGPM AHLLHGVHEQ NYVPHVMAYA ACIGANLGHC 490        500        510        520
APASSLKDKT HTCPPCPAPE LLGGPSVFLF PPKPKDTLMI 530        540        550        560
SRTPEVTCVV VDVSHEDPEV KFNWYVDGVE VHNAKTKPRE 570        580        590        600
EQYNSTYRVV SVLTVLHQDW LNGKEYKCKV SNKALPAPIE 610        620        630        640
KTISKAKGQP REPQVYTLPP SREEMTKNQV SLTCLVKGFY 650        660        670        680
PSDIAVEWES NGQPENNYKT TPPVLDSDGS FFLYSKLTVD 690        700        710        720
KSRWQQGNVF SCSVMHEALH NHYTQKSLSL SPGKDIDDDD

DDDDDD
```

In this embodiment, the polypeptide is composed of five portions. The first portion (sALP) containing amino acids L1-S485 is the soluble part of the human tissue non-specific alkaline phosphatase enzyme, which contains the catalytic function. The second portion contains amino acids L486-K487 as a linker. The third portion (Fc) containing amino acids $D_{488}$-K714 is the Fc part of the human immunoglobulin gamma 1 (IgG1) containing hinge, $CH_2$ and $CH_3$ domains. The fourth portion contains D715-I716 as a linker. The fifth portion contains amino acids D717-D726 ($D_{10}$), which is a bone targeting moiety that allows asfotase alfa to bind to the mineral phase of bone. In addition, each polypeptide chain contains six potential glycosylation sites and eleven cysteine (Cys) residues. Cys102 exists as free cysteine. Each polypeptide chain contains four intra-chain disulfide bonds between Cys122 and Cys184, Cys472 and Cys480, Cys528 and Cys588, and Cys634 and Cys692. The two polypeptide chains are connected by two inter-chain disulfide bonds between Cys493 on both chains and between Cys496 on both chains. In addition to these covalent structural features, mammalian alkaline phosphatases are thought to have four metal-binding sites on each polypeptide chain, including two sites for zinc, one site for magnesium and one site for calcium.

There are four known isozymes of ALP, namely tissue non-specific alkaline phosphatase (TNALP) further described below, placental alkaline phosphatase (PALP) (as described e.g., in GenBank Accession Nos. NP_112603 and NP_001623), germ cell alkaline phosphatase (GCALP) (as described, e.g., in GenBank Accession No. P10696) and intestinal alkaline phosphatase (IAP) (as described, e.g., in GenBank Accession No. NP_001622). These enzymes possess very similar three-dimensional structures. Each of their catalytic sites contains four metal-binding domains, for metal ions that are necessary for enzymatic activity, including two Zn and one Mg. These enzymes catalyze the hydrolysis of monoesters of phosphoric acid and also catalyze a transphosphorylation reaction in the presence of high concentrations of phosphate acceptors. Three known natural substrates for ALP (e.g., TNALP) include phosphoethanolamine (PEA), inorganic pyrophosphate (PPi) and pyridoxal 5'-phosphate (PLP) (Whyte et al., 1995 *J Clin Invest* 95:1440-1445). An alignment between these isozymes is shown in FIG. 30 of WO 2008/138131, the teachings of which are incorporated by reference herein in their entirety.

The alkaline phosphatase protein in this disclosure may comprise a dimer or multimers of any ALP protein, alone or in combination. Chimeric ALP proteins or fusion proteins may also be produced, such as the chimeric ALP protein that is described in Kiffer-Moreira et al. 2014 *PLoS One* 9:e89374, the entire teachings of which are incorporated by reference herein in its entirety.

In one particular embodiment, the alkaline phosphatase disclosed herein is encoded by a polynucleotide encoding a polypeptide comprising the sequence as set forth in SEQ ID NO: 1. In some embodiments, the alkaline phosphatase disclosed herein is encoded by a polynucleotide encoding a polypeptide comprising a sequence having 80%, 85%, 88%, 90%, 91%, 92%, 93%, 94%, 95%, 96%, 97%, 98% or 99% identity to SEQ ID NO: 1. In some embodiments, the alkaline phosphatase disclosed herein is encoded by a polynucleotide encoding a polypeptide comprising a sequence having 95% or 99% identity to SEQ ID NO: 1. In another embodiment, the alkaline phosphatase disclosed herein comprises the sequence as set forth in SEQ ID NO: 1.

TNALP

As indicated above, TNALP is a membrane-bound protein anchored through a glycolipid to its C-terminus (for human TNALP, see UniProtKB/Swiss-Prot Accession No. P05186). This glycolipid anchor (GPI) is added post translationally after removal of a hydrophobic C-terminal end which serves both as a temporary membrane anchor and as a signal for the addition of the GPI. Hence, in one embodiment a soluble human TNALP comprises a TNALP wherein the first amino acid of the hydrophobic C-terminal sequence, namely alanine, is replaced by a stop codon. The soluble TNALP (herein called sTNALP) so formed contains all amino acids of the native anchored form of TNALP that are necessary for the formation of the catalytic site but lacks the GPI membrane anchor. Known TNALPs include, e.g., human TNALP [GenBank Accession Nos. NP-000469, AAI10910, AAH90861, AAH66116, AAH21289, and AAI26166]; rhesus TNALP [GenBank Accession No. XP-001109717]; rat TNALP [GenBank Accession No. NP_037191]; dog TNALP [GenBank Accession No. AAF64516]; pig TNALP [GenBank Accession No. AAN64273], mouse TNALP [GenBank Accession No. NP_031457], bovine TNALP [GenBank Accession Nos. NP_789828, NP_776412, AAM 8209, and AAC33858], and cat TNALP [GenBank Accession No. NP_001036028].

As used herein, the terminology "extracellular domain" is meant to refer to any functional extracellular portion of the native protein (e.g., without the peptide signal). Recombinant sTNALP polypeptide retaining original amino acids 1 to 501 (18 to 501 when secreted), amino acids 1 to 502 (18 to 502 when secreted), amino acids 1 to 504 (18 to 504 when secreted), or amino acids 1 to 505 (18-505 when secreted) are enzymatically active (see Oda et al., 1999 *J. Biochem* 126:694-699). This indicates that amino acid residues can be removed from the C-terminal end of the native protein without affecting its enzymatic activity. Furthermore, the soluble human TNALP may comprise one or more amino acid substitutions, wherein such substitution(s) does not reduce or at least does not completely inhibit the enzymatic activity of the sTNALP. For example, certain mutations that are known to cause hypophosphatasia (HPP) are listed in PCT Publication No. WO 2008/138131 and should be avoided to maintain a functional sTNALP.

Negatively-Charged Peptide

The alkaline phosphatase protein of the present disclosure may comprise a target moiety which may specifically target the alkaline phosphatase protein to a pre-determined cell type, tissue, or organ. In some embodiments, such pre-determined cell type, tissue, or organ is bone tissues. Such bone-targeting moiety may include any known polypeptide, polynucleotide, or small molecule compounds known in the art. For example, negatively-charged peptides may be used as a bone-targeting moiety. In some embodiments, such negatively-charged peptides may be a poly-aspartate, polyglutamate, or combination thereof (e.g., a polypeptide comprising at least one aspartate and at least one glutamate, such as a negatively-charged peptide comprising a combination of aspartate and glutamate residues). In some embodiments, such negatively-charged peptides may be $D_6$, $D_7$, Ds, $D_9$, $D_{10}$, $D_{11}$, $D_{12}$, $D_{13}$, $D_{14}$, $D_{15}$, $D_{16}$, $D_{17}$, $D_{18}$, $D_{19}$, $D_{20}$, or a polyaspartate having more than 20 aspartates. In some embodiments, such negatively-charged peptides may be $E_6$, $E_7$, $E_8$, $E_9$, $E_{10}$, $E_{11}$, $E_{12}$, $E_{13}$, $E_{14}$, $E_{15}$, $E_{16}$, $E_{17}$, $E_{18}$, $E_{19}$, $E_{20}$, or a polyglutamate having more than 20 glutamates. In one embodiment, such negatively-charged peptides may comprise at least one selected from the group consisting of $D_{10}$ to $D_{16}$ or $E_{10}$ to $E_{16}$.

Spacer

In some embodiments, the alkaline phosphatase protein of the present disclosure comprises a spacer sequence between the ALP portion and the targeting moiety portion. In one embodiment, such alkaline phosphatase protein comprises a spacer sequence between the ALP (e.g., TNALP) portion and the negatively-charged peptide targeting moiety. Such spacer may be any polypeptide, polynucleotide, or small molecule compound. In some embodiments, such spacer may comprise fragment crystallizable region (Fc) fragments. Useful Fc fragments include Fc fragments of IgG that comprise the hinge, and the CH2 and $CH_3$ domains. Such IgG may be any of IgG-1, IgG-2, IgG-3, IgG-3 and IgG-4, or any combination thereof.

Without being limited to this theory, it is believed that the Fc fragment used in bone-targeted sALP fusion proteins (e.g., asfotase alfa) acts as a spacer, which allows the protein to be more efficiently folded given that the expression of sTNALP-Fc-$D_{10}$ was higher than that of sTNALP-$D_{10}$. One possible explanation is that the introduction of the Fc fragment alleviates the repulsive forces caused by the presence of the highly negatively-charged $D_{10}$ sequence added at the C-terminus of the sALP sequence exemplified herein. In some embodiments, the alkaline phosphatase protein described herein comprises a structure selected from the group consisting of: sALP-Fc-$D_{10}$, sALP-$D_{10}$-Fc, $D_{10}$-sALP-Fc, $D_{10}$-Fc-sALP, Fc-sALP-$D_{10}$, and Fc-$D_{10}$-sALP. In other embodiments, the $D_{10}$ in the above structures is substituted by other negatively-charged polypeptides (e.g., $D_8$, $D_{16}$, $E_{10}$, $E_8$, $E_{16}$, etc.).

Useful spacers for the present disclosure include, e.g., polypeptides comprising a Fc, and hydrophilic and flexible polypeptides able to alleviate the repulsive forces caused by the presence of the highly negatively-charged bone-targeting sequence (e.g., $D_{10}$) added at the C-terminus of the sALP sequence.

Dimers/Tetramers

In specific embodiments, the bone-targeted sALP fusion proteins of the present disclosure are associated so as to form dimers or tetramers.

In the dimeric configuration, the steric hindrance imposed by the formation of the interchain disulfide bonds is presumably preventing the association of sALP domains to associate into the dimeric minimal catalytically-active protein that is present in normal cells.

The bone-targeted sALP may further optionally comprise one or more additional amino acids 1) downstream from the negatively-charged peptide (e.g., the bone tag); and/or 2) between the negatively-charged peptide (e.g., the bone tag) and the Fc fragment; and/or 3) between the spacer (e.g., an Fc fragment) and the sALP fragment. This could occur, for example, when the cloning strategy used to produce the bone-targeting conjugate introduces exogenous amino acids in these locations. However the exogenous amino acids should be selected so as not to provide an additional GPI anchoring signal. The likelihood of a designed sequence being cleaved by the transamidase of the host cell can be predicted as described by Ikezawa, 2002 Glycosylphosphatidylinositol (GPI)-anchored proteins. *Biol Pharm Bull.* 25:409-17.

The present disclosure also encompasses a fusion protein that is post-translationally modified, such as by glycosylation including those expressly mentioned herein, acetylation, amidation, blockage, formylation, gamma-carboxyglutamic acid hydroxylation, methylation, phosphorylation, pyrrolidone carboxylic acid, and sulfation.

Asfotase Alfa

Asfotase alfa is a soluble Fc fusion protein consisting of two TNALP-Fc-$D_{10}$ polypeptides each with 726 amino acids as shown in SEQ ID NO: 1. Each polypeptide or monomer is composed of five portions. The first portion (sALP) containing amino acids L1-S485 is the soluble part of the human tissue non-specific alkaline phosphatase enzyme, which contains the catalytic function. The second portion contains amino acids L486-K487 as a linker. The third portion (Fc) containing amino acids D488-K714 is the Fc part of the human Immunoglobulin gamma 1 (IgG1) containing hinge, $CH_2$ and $CH_3$ domains. The fourth portion contains D715-I716 as a linker. The fifth portion contains amino acids D717-D726 ($D_{10}$), which is a bone targeting moiety that allows asfotase alfa to bind to the mineral phase of bone. In addition, each polypeptide chain contains six potential glycosylation sites and eleven cysteine (Cys) residues. Cys102 exists as free cysteine. Each polypeptide chain contains four intra-chain disulfide bonds between Cys122 and Cys184, Cys472 and Cys480, Cys528 and Cys588, and Cys634 and Cys692. The two polypeptide chains are connected by two inter-chain disulfide bonds between Cys493 on both chains and between Cys496 on both chains. In addition to these covalent structural features, mammalian alkaline phosphatases are thought to have four metal-binding sites on each polypeptide chain, including two sites for zinc, one site for magnesium and one site for calcium.

Asfotase alfa can also be characterized as follows. From the N-terminus to the C terminus, asfotase alfa comprises: (1) the soluble catalytic domain of human tissue non-specific alkaline phosphatase (TNSALP) (UniProtKB/Swiss-Prot Accession No. P05186), (2) the human immunoglobulin G1 Fc domain (UniProtKB/Swiss-Prot Accession No. P01857) and (3) a deca-aspartate peptide ($D_{10}$) used as a bone-targeting domain (Nishioka et al. 2006 *Mol Genet Metab* 88:244-255). The protein associates into a homo-dimer from two primary protein sequences. This fusion protein contains 6 confirmed complex N-glycosylation sites. Five of these N-glycosylation sites are located on the sALP domain and one on the Fc domain. Another important post-translational modification present on asfotase alfa is the presence of disulfide bridges stabilizing the enzyme and the Fc-domain structure. A total of 4 intra-molecular disulfide bridges are present per monomer and 2 inter-molecular disulfide bridges are present in the dimer. One cysteine of the alkaline phosphatase domain is free.

Asfotase alfa has been used as an enzyme-replacement therapy for the treatment of hypophosphatasia (HPP). In patients with HPP, loss-of-function mutation(s) in the gene encoding TNSALP causes a deficiency in TNSALP enzymatic activity, which leads to elevated circulating levels of substrates, such as inorganic pyrophosphate (PPi) and pyridoxal-5'-phosphate (PLP). Administration of asfotase alfa to patients with HPP cleaves PPi, releasing inorganic phosphate for combination with calcium, thereby promoting hydroxyapatite crystal formation and bone mineralization, and restoring a normal skeletal phenotype. For more details on asfotase alfa and its uses in treatment, see PCT Publication Nos. WO 2005/103263 and WO 2008/138131

In some embodiments, the method provides an alkaline phosphatase (asfotase alfa) having improved enzymatic activity of the produced alkaline phosphatase (e.g., asfotase alfa) relative to an alkaline phosphatase produced by conventional means, by minimizing the concentration of metal ions having potential negative impact on activity or increasing the concentration of metal ions having potential positive impact on activity or both as described herein. Activity may be measured by any known method. Such methods include, e.g., those in vitro and in vivo assays measuring the enzymatic activity of the produced alkaline phosphatase (e.g., asfotase alfa) to substrates of an alkaline phosphatase, such as phosphoethanolamine (PEA), inorganic pyrophosphate (PPi) and pyridoxal 5'-phosphate (PLP).

In some embodiments, the alkaline phosphatase disclosed herein is encoded by a first polynucleotide which hybridizes under high stringency conditions to a second polynucleotide comparing the sequence completely complementary to a third polynucleotide encoding a polypeptide comprising the sequence as set forth in SEQ ID NO: 1. Such high stringency conditions may comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for 5 minutes.

Manufacturing Process

The alkaline phosphatase protein described herein (e.g., asfotase alfa) may be produced by mammalian or other cells, particularly CHO cells, using methods known in the art. Such cells may be grown in culture dishes, flask glasses, or bioreactors. Specific processes for cell culture and producing recombinant proteins are known in the art, such as described in Nelson and Geyer, 1991 *Bioprocess Technol.* 13:112-143 and Rea et al., *Supplement to BioPharm International March* 2008, 20-25. Exemplary bioreactors include batch, fed-batch, and continuous reactors. In some embodiments, the alkaline phosphatase protein is produced in a fed-batch bioreactor.

Cell culture processes have variability caused by, for example, variable physicochemical environment, including but not limited to, changes in pH, temperature, temperature changes, timing of temperature changes, cell culture media composition, cell culture nutrient supplements, raw material lot-to-lot variation, medium filtration material, bioreactor scale difference, gassing strategy (air, oxygen, and carbon dioxide), etc. As disclosed herein, the yield, relative activity profile, and glycosylation profile of manufactured alkaline phosphatase protein may be affected and may be controlled within particular values by alterations in one or more of these parameters.

For recombinant protein production in cell culture, the recombinant gene with the necessary transcriptional regulatory elements is first transferred to a host cell by methods known in the biotechnological arts. Optionally, a second gene is transferred that confers to recipient cells a selective advantage. In the presence of the selection agent, which may be applied a few days after gene transfer, only those cells that express the selector gene survive. Two exemplary genes for such selection are dihydrofolate reductase (DHFR), an enzyme involved in nucleotide metabolism, and glutamine synthetase (GS). In both cases, selection occurs in the absence of the appropriate metabolite (hypoxanthine and thymidine, in the case of DHFR, and glutamine in the case of GS), preventing growth of any nontransformed cells. In general, for efficient expression of the recombinant protein, it is not important whether the biopharmaceutical-encoding gene and selector genes are on the same plasmid or not.

Following selection, surviving cells may be transferred as single cells to a second cultivation vessel, and the cultures are expanded to produce clonal populations. Eventually, individual clones are evaluated for recombinant protein expression, with the highest producers being retained for further cultivation and analysis. From these candidates, one cell line with the appropriate growth and productivity characteristics is chosen for production of the recombinant protein. A cultivation process is then developed that is determined by the production needs and the requirements of the final product.

Cells

Any mammalian cell or non-mammalian cell type, which can be cultured to produce a polypeptide, may be utilized in accordance with the present disclosure. Non-limiting examples of mammalian cells that may be used include, e.g., Chinese hamster ovary cells+/−DHFR (CHO, Urlaub and Chasin, 1980 *Proc. Natl. Acad. Sci. USA,* 77:4216); BALB/c mouse myeloma line (NSO/1, ECACC Accession No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., 1977 *J. Gen Virol.,* 36:59); baby hamster kidney cells (BHK, ATCC CCL 10); mouse Sertoli cells (TM4, *Mather, Biol. Reprod.,* 23:243-251 (1980)); monkey kidney cells (CV1 ATCC CCL 70); African green monkey kidney cells (VERO-76, ATCC CRL-I 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 1982, *Annals N.Y. Acad. Sci.* 383:44-68); MRC 5 cells; FS4 cells; and a human hepatoma line (Hep G2). In a particular embodiment, culturing and expression of polypeptides and proteins occurs from a Chinese Hamster Ovary (CHO) cell line.

Additionally, any number of commercially and non-commercially available hybridoma cell lines that express polypeptides or proteins may be utilized in accordance with the present disclosure. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Seeding Density

In the present disclosure, Chinese Hamster Ovary (CHO) cells are inoculated, i.e., seeded, into the culture medium. Various seeding densities can be used. In some embodiments, a seeding density of $1.0 \times 10^4$ cells/mL to $1.0 \times 10^7$ cells/mL can be used. In some embodiments, a seeding density of $1.0 \times 10^5$ cells/mL to $1.0 \times 10^6$ cells/mL can be used. In some embodiments, a seeding density of $4.0 \times 10^5$ cells/mL to $8.0 \times 10^5$ cells/mL can be used. In some embodiments, increased seeding density can impact fragmentation of asfotase alfa quality, as measured by SEC. In some embodiments, the seeding density is controlled when inoculating in order to reduce the risk of fragment generation.

Temperature

Prior results indicated that temperature may have an impact on several parameters including growth rate, aggregation, fragmentation, and TSAC. In some embodiments, the temperature remains constant when culturing the CHO cells in the culture medium. In some embodiments, the temperature is about 30° C. to about 40° C., or about 35° C. to about 40° C., or about 37° C. to about 39° C. when culturing the CHO cells in the culture medium. In some embodiments, the temperature is about 30° C., about 30.5° C., about 31° C., about 31.5° C., about 32° C., about 32.5° C., about 33° C., about 33.5° C., about 34° C., about 34.5° C., about 35° C., about 35.5° C., about 36° C., about 36.5° C., about 37° C., about 37.5° C., about 38° C., about 38.5° C., about 39° C., about 39.5° C., or about 40° C. when culturing the CHO cells in the culture medium. In some embodiments, the temperature is constant for 40 to 200 hours after inoculation. In some embodiments, the temperature is constant for 50 to 150 hours, or 60 to 140 hours, or 70 to 130 hours, or 80 to 120 hours, or 90 to 110 hours after inoculation. In some embodiments, the temperature is constant for 80 to 120 hours after inoculation. In some embodiments, the temperature is constant for 90 hours, 92 hours, 94 hours, 96 hours, 98 hours, 100 hours, 102 hours, 104 hours, 106 hours, 108 hours or 110 hours after inoculation.

Temperature Shifting

Run times of cell culture processes, especially non-continuous processes (e.g., fed-batch processes in bioreactors), are usually limited by the remaining viability of the cells, which typically declines over the course of the run. Therefore, extending the length of time for cell viability is desired for improving recombination protein production. Product quality concerns also offer a motivation for minimizing decreases in viable cell density and maintaining high cell viability, as cell death can release sialidases to the culture supernatant, which may reduce the sialic acid content of the protein expressed. Protein purification concerns offer yet another motivation for minimizing decreases in viable cell density and maintaining high cell viability. Cell debris and the contents of dead cells in the culture can negatively impact one's ability to isolate and/or purify the protein product at the end of the culturing run. Thus, by keeping cells viable for a longer period of time in culture, there is a reduction in the contamination of the culture medium by cellular proteins and enzymes (e.g., cellular proteases and sialidases) that may cause degradation and ultimate reduction in the quality of the desired glycoprotein produced by the cells.

Many methods may be applied to achieve high cell viability in cell cultures. One involves lowering culture temperature following initial culturing at a normal temperature. For example, see Ressler et al., 1996, *Enzyme and Microbial Technology* 18:423-427). Generally, the mammalian or other types of cells capable of expressing a protein of interest are first grown under a normal temperature to increase cell numbers. Such "normal" temperatures for each cell type are generally around 37° C. (e.g., from about 35° C. to about 39° C., including, for example, 35.0° C., 35.5° C., 36.0° C., 36.5° C., 37.0° C., 37.5° C., 38.0° C., 38.5° C., and/or 39.0° C.). In one particular embodiment, the temperature for producing asfotase alfa is first set at about 37° C. When a reasonably high cell density is reached, the culturing temperature for the whole cell culture can then be shifted (e.g., decreased) to promote protein production. In most cases lowering temperature shifts the cells towards the non-growth G1 portion of the cell cycle, which may increase cell density and viability, as compared to the previous higher-temperature environment. In addition, a lower temperature may also promote recombinant protein production by increasing the cellular protein production rate, facilitating protein post-translational modification (e.g., glycosylation), decreasing fragmentation or aggregation of newly-produced proteins, facilitating protein folding and formation of 3D structure (thus maintaining activity), and/or decreasing degradation of newly produced proteins. In some embodiments, the temperature is decreased 3° C., 4° C., 5° C., 6° C., 7° C., 8° C., 9° C., or 10° C. In some embodiments, the temperature is decreased to about 27° C., 28° C., 29° C., 30° C., 31° C., 32° C., 33° C., 34° C., or 35° C. In some embodiments, the lower temperature is from about 30° C. to about 35° C. (e.g., 30.0° C., 30.5° C., 31.0° C., 31.5° C., 32.0° C., 32.5° C., 33.0° C., 33.5° C., 34.0° C., 34.5° C., and/or 35.0° C.). In other embodiments, the temperature for producing asfotase alfa is first set to from about 35.0° C. to about 39.0° C. and then shifted to from about 30.0° C. to about 35.0° C. In one embodiment, the temperature for producing asfotase alfa is first set at about 37.0° C. and then shifted to about 30° C. In another embodiment, the temperature for producing asfotase alfa is first set at about 36.5° C. and then shifted to about 33° C. In yet another embodiment, the temperature for producing asfotase alfa is first set at about 37.0° C. and then shifted to about 33° C. In yet a further embodiment, the temperature for producing asfotase alfa is first set at about 36.5° C. and then shifted to about 30° C. In other embodiments, multiple (e.g., more than one) steps of temperature shifting may be applied.

The time for maintaining the culture at a particular temperature prior to shifting to a different temperature may be determined to achieve a sufficient (or desired) cell density while maintaining cell viability and an ability to produce the protein of interest. In some embodiments, the cell culture is grown under the first temperature until the viable cell density reaches about $10^5$ cells/mL to about $10^7$ cells/mL (e.g., $1\times10^5$, $1.5\times10^5$, $2.0\times10^5$, $2.5\times10^5$, $3.0\times10^5$, $3.5\times10^5$, $4.0\times10^5$, $4.5\times10^5$, $5.0\times10^5$, $5.5\times10^5$, $6.0\times10^5$, $6.5\times10^5$, $7.0\times10^5$, $7.5\times10^5$, $8.0\times10^5$, $8.5\times10^5$, $9.0\times10^5$, $9.5\times10^5$, $1.0\times10^6$, $1.5\times10^6$, $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, $7.0\times10^6$, $7.5\times10^6$, $8.0\times10^6$, $8.5\times10^6$, $9.0\times10^6$, $9.5\times10^6$, $1\times10^7$ cell/mL, or more) before shifting to a different temperature. In one embodiment, the cell culture is grown under the first temperature until the viable cell density reaches about 2.5 to about $3.4\times10^6$ cells/mL before shifting to a different temperature. In another embodiment, the cell culture is grown under the first temperature until the viable cell density reaches about 2.5 to about $3.2\times10^6$ cells/mL before shifting to a different temperature. In yet another embodiment, the cell culture is grown under the first temperature until the viable cell density reaches about 2.5 to about $2.8\times10^6$ cells/mL before shifting to a different temperature.

In some embodiments, the method of the present disclosure provides the temperature shift occurs 50 to 150 hours, or 60 to 140 hours, or 70 to 130 hours, or 80 to 120 hours, or 90 to 110 hours after inoculation. In some embodiments, the method of the present disclosure provides the temperature decreased about 80 hours to 150 hours after inoculation, about 90 hours to 100 hours after inoculation or about 96 hours after inoculation. In some embodiments, the temperature shift occurs 80 to 120 hours after inoculation. In some embodiments, the temperature shift occurs 90 hours, 92 hours, 94 hours, 96 hours, 98 hours, 100 hours, 102 hours, 104 hours, 106 hours, 108 hours or 110 hours after inoculation. In some embodiments, the temperature after the temperature shift is maintained until the CHO cells are harvested.

pH

Alteration of the pH of the growth medium in cell culture may affect cellular proteolytic activity, secretion, and protein production levels. Most of the cell lines grow well at about pH 7-8. Although optimum pH for cell growth varies relatively little among different cell strains, some normal fibroblast cell lines perform best at a pH 7.0-7.7 and transformed cells typically perform best at a pH of 7.0-7.4 (Eagle, 1973 The effect of environmental pH on the growth of normal and malignant cells. J Cell Physiol 82:1-8). In some embodiments, the pH of the culture medium for producing asfotase alfa is about pH 6.5-7.7 (e.g., 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.39, 7.40, 7.45, 7.50, 7.55, 7.60, 7.65, or 7.70).

Culture Medium

In some embodiments, batch culture is used, wherein no additional culture medium is added after inoculation. In some embodiments, fed batch is used, wherein one or more boluses of culture medium are added after inoculation. In some embodiments, two, three, four, five or six boluses of culture medium are added after inoculation.

In various embodiments, alkaline phosphatase (e.g., asfotase alfa) is produced by a process in which extra boluses of culture medium are added to the production bioreactor. For example, one, two, three, four, five, six, or more boluses of culture medium may be added. In one particular embodiment, three boluses of culture medium are added. In various embodiments, such extra boluses of culture medium may be added in various amounts. For example, such boluses of culture medium may be added in an amount of about 20%, 25%, 30%, 33%, 40%, 45%, 50%, 60%, 67%, 70%, 75%, 80%, 90%, 100%, 110%, 120%, 125%, 130%, 133%, 140%, 150%, 160%, 167%, 170%, 175%, 180%, 190%, 200%, or more, of the original volume of culture medium in the production bioreactor. In one particular embodiment, such boluses of culture medium may be added in an amount of about 33%, 67%, 100%, or 133% of the original volume. In various embodiments, such addition of extra boluses may occur at various times during the cell growth or protein production period. For example, boluses may be added at day 1, day 2, day 3, day 4, day 5, day 6, day 7, day 8, day 9, day 10, day 11, day 12, or later in the process. In one particular embodiment, such boluses of culture medium may be added in every other day (e.g., at (1) day 3, day 5, and day 7; (2) day 4, day 6, and day 8; or (3) day 5, day 7, and day 9. In practice, the frequency, amount, time point, and other parameters of bolus supplements of culture medium may be combined freely according to the above limitation and determined by experimental practice.

Various culture mediums are available commercially. In some embodiments, the culture medium is selected from the group consisting of EX-CELL® 302 Serum-Free Medium; CD DG44 Medium; BD Select™ Medium; SFM4CHO Medium, or a combination thereof. In some embodiments, the culture medium comprises a combination of commercially available mediums, e.g., SFM4CHO Medium and BD Select™ Medium. In some embodiments, the culture medium comprises a combination of commercially available mediums, e.g., SFM4CHO Medium and BD Select™ Medium, at a ratio selected from 90/10, 80/20, 75/25, 70/30, 60/40, or 50/50.

Nutrient Supplement

Various nutrient supplements, also referred to as "feed media," are commercially available and are known to those of skill in the art. Nutrient supplements include a media (distinct from the culture media) added to a cell culture after innocuation has occurred. In some instances, the nutrient supplement can be used to replace nutrients consumed by the growing cells in the culture. In some embodiments, the nutrient supplement is added to optimize production of a desired protein, or to optimize activity of a desired protein. Numerous nutrient supplements have been developed and are available commercially. While the expressed purpose of the nutrient supplements is to increase an aspect of process development, no universal nutrient supplement exists that works for all cells and/or all proteins produced. The selection of a scalable and appropriate cell culture nutrient supplement that can work in combination with the desired cell line, protein produced and a given base medium to achieve the desired titer and growth characteristics is not routine. The typical approach of screening multiple commercially available nutrient supplements and identifying the most appropriate supplement with a specific cell line, specific protein produced and base medium combination may not be successful due to the myriad of variables present in the cell culture process. In some embodiments, the nutrient supplement is selected from the group consisting of Efficient Feed C+ AGT™ Supplement (Thermo Fisher Scientific, Waltham, MA), a combination of Cell Boost™ 2+Cell Boost™ 4 (GE Healthcare, Sweden), a combination of Cell Boost™ 2+Cell Boost™ 5 (GE Healthcare, Sweden), Cell Boost™ 6 (GE Healthcare, Sweden), and Cell Boost™ 7a+Cell Boost™ 7b (GE Healthcare, Sweden), or combinations thereof.

Cell Boost™ 7a can be described as a first animal-derived component-free (ADCF) nutrient supplement comprising one or more amino acids, vitamins, salts, trace elements, poloxamer and glucose, wherein the first ADCF nutrient supplement does not comprise hypoxanthine, thymidine, insulin, L-glutamine, growth factors, peptides, proteins, hydrolysates, phenol red and 2-mercaptoethanol. Cell Boost™ 7a is a chemically defined supplement. The phrase "animal-derived component-free" or "ADCF" refers to a supplement in which no ingredients are derived directly from an animal source, e.g., are not derived from a bovine source. In some embodiments, the nutrient supplement is Cell Boost™ 7a.

Cell Boost™ 7b can be described as a second ADCF nutrient supplement comprising one or more amino acids, wherein the second ADCF nutrient supplement lacks hypoxanthine, thymidine, insulin, L-glutamine, growth factors, peptides, proteins, hydrolysates, phenol red, 2-mercaptoethanol and poloxamer. Cell Boost™ 7b is a chemically defined supplement. In some embodiments, the nutrient supplement is Cell Boost™ 7b.

In some embodiments, combinations of commercially available nutrient supplements are used. The term "nutrient supplement" refers to both a single nutrient supplement, as well as combinations of nutrient supplements. For example, in some embodiments a combination of nutrient supplements includes a combination of Cell Boost™ 7a and Cell Boost™ 7b.

In various embodiments, alkaline phosphatase (e.g., asfotase alfa) is produced by a process in which extra additions of nutrient supplement are added to the production bioreactor. In some embodiments, the nutrient supplement is added over a period of time, e.g., over a period of time ranging from 1 minute to 2 hours. In some embodiments, the nutrient supplement is added in a bolus. For example, one, two, three, four, five, six, or more boluses of nutrient supplement may be added. In some embodiments, the nutrient supplement is added at more than 2 different times, e.g., 2 to 6 different times. In various embodiments, such extra boluses of nutrient supplement may be added in various amounts. For example, such boluses of nutrient supplement may be added in an amount of about 1% to 20%, 1% to 10% or 1% to 5% (w/v) of the original volume of culture medium in the production bioreactor. In one particular embodiment, such boluses of nutrient supplement may be added in an amount of 1% to 20%, 1% to 10% or 1% to 5% (w/v) of the original volume.

In some embodiments, a combination of nutrient supplements is used, and the first nutrient supplement, e.g., Cell Boost™ 7a, is added at a concentriaton of 0.5% to 4% (w/v) of the culture medium. In some embodiments, a combination of nutrient supplements is used, and the second nutrient supplement, e.g., Cell Boost™ 7b, is added at a concentriaton of 0.05% to 0.8% (w/v) of the culture medium. In specific embodiments wherein a combination of nutrient supplements include Cell Boost™ 7a and Cell Boost™ 7b, a boluses of nutrient supplement may be added in an amount of 1% to 20%, 1% to 10% or 1% to 5% (w/v) of the original volume.

In various embodiments, such addition of extra boluses may occur at various times after inoculation. For example, boluses may be added at day 1, day 2, day 3, day 4, day 5, day 6, day 7, day 8, day 9, day 10, day 11, day 12, or later after inoculation. In practice, the frequency, amount, time point, and other parameters of bolus supplements of nutrient supplement may be combined freely according to the above limitation and determined by experimental practice.

In some embodiments, the method disclosed herein further comprises adding zinc into said culture medium during production of the recombinant polypeptide. In some embodiments, zinc may be added to provide a zinc concentration of from about 1 to about 300 µM in said culture medium. In one embodiment, zinc may be added to provide a zinc concentration of from about 10 to about 200 µM (e.g., 10, 20, 30, 40, 50, 60, 70, 80, 90, 100, 110, 120, 130, 140, or 150 µM) in the culture medium. In some embodiments, zinc is added to provide a zinc concentration in the culture medium of from about 25 µM to about 150 µM, or about 60 µM to about 150 µM. In one embodiment, zinc is added to provide a zinc concentration in the culture medium of from about about 30, 60, or 90 µM of zinc. In some embodiments, the zinc is added into said culture medium in a bolus, continuously, semi-continuously, or combinations thereof. In some embodiments, zinc is added one day, two days, three days, four days, five days, six days, seven days, eight days, nine days, ten days, eleven days, twelve days, and/or thirteen days after inoculation.

Harvest

Prior studies suggested that delaying harvest timing was associated with a viability and TSAC decline, so harvest timing can have a potential impact on other CQAs. In various embodiments, alkaline phosphatase (e.g., asfotase alfa) is harvested at a time point of about 200 hr, 210 hr, 220 hr, 230 hr, 240 hr, 250 hr, 260 hr, 264 hr, 270 hr, 280 hr, 288 hr (i.e., 12 days), or more than 12 days.

Downstream Processes

The term "downstream process(es)" used herein is generally referred to the whole or part(s) of the processes for recovery and purification of the alkaline phosphatases (e.g., asfotase alfa) produced from sources such as culture cells or fermentation broth.

Generally, downstream processing brings a product from its natural state as a component of a tissue, cell or fermentation broth through progressive improvements in purity and concentration. For example, the removal of insolubles may be the first step, which involves the capture of the product as a solute in a particulate-free liquid (e.g., separating cells, cell debris or other particulate matter from fermentation broth). Exemplary operations to achieve this include, e.g., filtration, centrifugation, sedimentation, precipitation, flocculation, electro-precipitation, gravity settling, etc. Additional operations may include, e.g., grinding, homogenization, or leaching, for recovering products from solid sources, such as plant and animal tissues. The second step may be a "product-isolation" step, which removes components whose properties vary markedly from that of the desired product. For most products, water is the chief impurity and isolation steps are designed to remove most of it, reducing the volume of material to be handled and concentrating the product. Solvent extraction, adsorption, ultrafiltration, and precipitation may be used alone or in combinations for this step. The next step is about product purification, which separates contaminants that resemble the product very closely in physical and chemical properties. Possible purification methods include, e.g., affinity, ion-exchange chromatography, hydrophobic interaction chromatography, mixed-mode chromatography, size exclusion, reversed phase chromatography, ultrafiltration-diafiltration, crystallization and fractional precipitation. In some embodiments, the downstream processes comprise at least one of harvest clarification, ultrafiltration, diafiltration, viral inactivation, affinity capture, and combinations thereof. Downstream processes are described herein.

Determination of Total Sialic Acid Content

Commercial methods of carbohydrate quantification are available, e.g., from ThermoFisher. Generally, TSAC is released from a glycoprotein, e.g., asfotase alfa, using acid hydrolysis, and released sugars/TSAC are detected via electrochemical detection using column chromatography such as High-Performance Anion-Exchange Chromatography with Pulsed Amperometric Detection technique (HPAE-PAD). The resulting levels are quantified per mole against an internal standard and expressed as a function of the total mole protein.

In some embodiments, the methods described herein further comprise measuring the total sialic acid content (TSAC) of the recombinant alkaline phosphatase. As described herein, TSAC impacts the half-life of the recombinant alkaline phosphatase in physiological conditions, and thus serves as a critical quality attribute for recombinantly-produced alkaline phosphatases such as, e.g., asfotase alfa. Tight control of the TSAC range is important for reproducibility and cGMP. In some embodiments, the TSAC is about 0.8 mol/mol to about 4.0 mol/mol recombinant alkaline phosphatase. In some embodiments, the TSAC is about 0.9 mol/mol to about 3.0 mol/mol recombinant alkaline phosphatase. In some embodiments, the TSAC is about 1.0 mol/mol to about 2.8 mol/mol recombinant alkaline phosphatase. In some embodiments, the TSAC is about 1.2 mol/mol to about 3.0 mol/mol recombinant alkaline phosphatase. In some embodiments, the TSAC is about 1.2 mol/mol to about 2.4 mol/mol recombinant alkaline phosphatase. In some embodiments, the TSAC is about 0.9 mol/mol, about 1.0 mol/mol, about 1.1 mol/mol, about 1.2 mol/mol, about 1.3 mol/mol, about 1.4 mol/mol, about 1.5 mol/mol, about 1.6 mol/mol, about 1.7 mol/mol, about 1.8 mol/mol, about 1.9 mol/mol, about 2.0 mol/mol, about 2.1 mol/mol, about 2.2 mol/mol, about 2.3 mol/mol, about 2.4 mol/mol, about 2.5 mol/mol, about 2.6 mol/mol, about 2.7 mol/mol, about 2.8 mol/mol, about 2.9 mol/mol, or about 3.0 mol/mol recombinant alkaline phosphatase.

In some embodiments, the TSAC of recombinant alkaline phosphatase decreases during downstream processing. In some embodiments, the TSAC of recombinant alkaline phosphatases decreases as a result of sialidase enzymes present in the solution containing recombinant alkaline phosphatase, e.g., the cell culture, the HCCF, and/or the UFDF filtration pool. In some embodiments, sialidases are selectively removed from the cell culture, the HCCF, and/or the UFDF filtration pool to achieve a TSAC of about 0.9 mol/mol to about 3.0 mol/mol recombinant alkaline phosphatase. Sialidases can be selectively removed by, e.g., one or a combination of sialidase-specific inhibitors, antibodies, ion exchange and/or affinity chromatography, immunoprecipitation, and the like.

In some embodiments, sialic acid moieties are added to recombinant alkaline phosphatase by sialyltransferase enzymes present in the solution containing recombinant alkaline phosphatase, e.g., the cell culture, the HCCF, and/or the UFDF filtration pool. In some embodiments, recombinant sialyltransferases are added exogenously to the cell culture, the HCCF, and/or the UFDF filtration pool to achieve a TSAC of about 0.9 to about 3.0 mol/mol recombinant alkaline phosphatase.

Determination of Recombinant Alkaline Phosphatase Activity

In some embodiments, the methods described herein further comprise measuring recombinant alkaline phosphatase activity. In some embodiments, the activity is selected from a method selected from at least one of a pNPP-based alkaline phosphatase enzymatic assay and an inorganic pyrophosphate (PPi) hydrolysis assay. In some embodiments, at least one of the recombinant alkaline phosphatase Kcat and Km values increases in an inorganic pyrophosphate (PPi) hydrolysis assay. In some embodiments, the method comprises determining an integral of viable cell concentration (IVCC).

The last step may be used for product polishing, the processes which culminate with packaging of the product in a form that is stable, easily transportable and convenient. Storage at 2-8° C., freezing at −20° C. to −80° C., crystallization, desiccation, lyophilization, freeze-drying and spray drying are exemplary methods in this final step. Depending on the product and its intended use, product polishing may also sterilize the product and remove or deactivate trace contaminants (e.g., viruses, endotoxins, metabolic waste products, and pyrogens), which may compromise product safety.

Product recovery methods may combine two or more steps discussed herein. For example, expanded bed adsorption (EBA) accomplishes removal of insolubles and product isolation in a single step. For a review of EBA, see Kennedy, *Curr Protoc Protein Sci.* 2005 June; Chapter 8: Unit 8.8. In addition, affinity chromatography often isolates and purifies in a single step.

For a review of downstream processes for purifying a recombinant protein produced in culture cells, see Rea, 2008 Solutions for Purification of Fc-fusion Proteins. *BioPharm Int. Supplements March* 2:20-25. The downstream processes for alkaline phosphatases disclosed herein may include at least one, or any combination, of exemplary step described herein.

Harvest Clarification Process

In some embodiments of the method, the recombinant alkaline phosphatase is isolated from the cell culture by at least one purification step to form harvest clarified culture fluid (HCCF), i.e., a "harvesting" step or harvest clarification step. "Harvesting" the cell culture typically refers to the process of collecting the cell culture from the culture container, e.g., a bioreactor. In some embodiments, the at least one purification step comprises at least one of filtration, centrifugation, and combinations thereof. In some embodiments, the harvest clarification step comprises centrifuging and/or filtering the harvested cell culture in order to remove cells and cellular debris (e.g., insoluble biomaterials) to recover the product, i.e., the recombinant alkaline phosphatase. In some embodiments, the cells and cellular debris are removed in order to yield a clarified, filtered fluid suitable for chromatography. In some embodiments, the clarified, filtered fluid is known as harvest clarified culture fluid, or HCCF. In some embodiments, the cell culture is subjected to a combination of centrifugation and depth filtration to generate the HCCF. Possible used solutions in this step may include a recovery buffer (e.g., 50 mM Sodium Phosphate, 100 mM NaCl, pH 7.50). The composition of suitable recovery buffers may be selected by the skilled artisan.

In some embodiments, the HCCF has a total sialic acid content (TSAC) of from about 2.1 mol/mol to about 4.3 mol/mol. In some embodiments, the HCCF has a TSAC of from about 2.2 mol/mol to about 3.6 mol/mol. In some embodiments, the HCCF has a TSAC of from about 2.2 mol/mol to about 3.4 mol/mol. In some embodiments, the HCCF has a TSAC of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, or about 4.5 mol/mol.

Post-Harvest Ultrafiltration and/or Diafiltration

In some embodiments of the method, an additional purification step is performed after the at least one purification step to form a filtration pool, also known as an "UFDF pool" or "UFDF." In some embodiments, the at least one purification step is for concentration and buffer dilution. In some embodiments, the at least one purification step comprises at least one of harvest clarification, filtration, ultrafiltration, diafiltration, viral inactivation, affinity capture, and combinations thereof. In some embodiments, the at least one purification step comprises ultrafiltration (UF) and/or diafiltration (DF). Exemplary steps for the UF process include, e.g., pre-use cleaning/storage of the filter membrane, post-clean/post-storage flush, equilibration (e.g., with a buffer containing 50 mM sodium phosphate, 100 mM NaCl, pH 7.50), loading, concentration, dilution/flush/recovery (e.g., with a buffer containing 50 mM sodium phosphate, 100 mM NaCl, pH 7.50), and post-use flush/clean/storage of the filter membrane.

In some embodiments, after UF/DF, the UFDF is diluted to a protein concentration of about 1.7 g/L to about 5.3 g/L, then maintained at about 13° C. to about 27° C. for about 1 to about 60 hours, prior to storage and/or further purification. "Holding" or "maintaining" the UFDF, as used herein, refers to the UFDF being kept at the same temperature (within ±about 1° C.) for a target length of time, i.e., the "hold time" (within ±about 2 hours). In some embodiments, the UFDF is held in order to serve as a control point in the recombinant alkaline phosphatase production process. In some embodiments, the UFDF is held in order to ensure uniform product quality. In some embodiments, the UFDF is held in order to facilitate downstream processing.

In some embodiments, the TSAC of the recombinant alkaline phosphatase decreases during the UFDF hold time. In some embodiments, the TSAC decline is correlated with the protein concentration, length of time, and/or temperature during the UFDF hold time.

In some embodiments, the start of the UFDF hold time is immediately after the end of the chromatography step. In some embodiments, the start of the UFDF hold time is immediately after the end of the UF/DF. In some embodiments, the start of the UFDF hold time is immediately after the completion of a recirculation at the end of the UF/DF step. In some embodiments, the start of the UFDF hold time is immediately after the UF/DF product filtration and transfer is completed.

In some embodiments, the UFDF is diluted to achieve a desired protein concentration. In some embodiments, the UFDF has a protein concentration of about 1.0 g/L to about 6.0 g/L. In some embodiments, the UFDF has a protein concentration of about 1.7 g/L to about 5.3 g/L. In some embodiments, the UFDF has a protein concentration of about 2.0 g/L to about 5.0 g/L. In some embodiments, the UFDF has a protein concentration of about 2.3 g/L to about 4.3 g/L. In some embodiments, the UFDF has a protein concentration of about 3.0 g/L to about 4.5 g/L. In some embodiments, the UFDF has a protein concentration of about 3.3 g/L to about 4.1 g/L. In some embodiments, the UFDF has a protein concentration of about 2.0 g/L, about 2.1 g/L, about 2.2 g/L, about 2.3 g/L, about 2.4 g/L, about 2.5 g/L, about 2.6 g/l, about 2.7 g/L, about 2.8 g/L, about 2.9 g/L, about 3.0 g/L, about 3.1 g/L, about 3.2 g/L, about 3.3 g/L, about 3.4 g/L, about 3.5 g/L, about 3.6 g/L, about 3.7 g/L, about 3.8 g/L, about 3.9 g/L, about 4.0 g/L, about 4.1 g/L, about 4.2 g/L, about 4.3 g/L, about 4.4 g/L, or about 4.5 g/L.

In some embodiments, the UFDF comprises a combination of recombinant alkaline phosphatase and other proteins. In some embodiments, the UFDF has an alkaline phosphatase concentration of about 2.0 g/L to about 6.0 g/L. In some embodiments, the UFDF has an alkaline phosphatase concentration of about 2.5 g/L to about 5.0 g/L. In some embodiments, the UFDF has an alkaline phosphatase concentration of about 3.0 g/L to about 4.5 g/L. In some embodiments, the UFDF has an alkaline phosphatase concentration of about 3.3 g/L to about 4.1 g/L. In some embodiments, the UFDF has an alkaline phosphatase concentration of about 3.0 g/L, about 3.1 g/L, about 3.2 g/L, about 3.3 g/L, about 3.4 g/L, about 3.5 g/L, about 3.6 g/L, about 3.7 g/L, about 3.8 g/L, about 3.9 g/L, about 4.0 g/L, about 4.1 g/L, about 4.2 g/L, about 4.3 g/L, about 4.4 g/L, or about 4.5 g/L.

In some embodiments, the UFDF is held for about 1 hour to about 60 hours. In some embodiments, the UFDF is held for about 10 hours to about 50 hours. In some embodiments, the UFDF is held for about 12 hours to about 48 hours. In some embodiments, the UFDF is held for about 14 hours to about 42 hours. In some embodiments, the UFDF is held for about 17 hours to about 34 hours. In some embodiments, the UFDF is held for about 19 hours to about 33 hours. In some embodiments, the UFDF is held for about 25 to about 38 hours. In some embodiments, the UFDF is held for about 29 to about 35 hours. In some embodiments, the UFDF is held for about 12 hours, about 13 hours, about 14 hours, about 15 hours, about 16 hours, about 17 hours, about 18 hours, about 19 hours, or about 20 hours. In some embodiments, the UFDF is held for about 29 hours, about 30 hours, about 31 hours, about 32 hours, about 33 hours, about 34 hours, or about 35 hours. In some embodiments, the UFDF is held for about 42 hours, about 43 hours, about 44 hours, about 45 hours, about 46 hours, about 47 hours, or about 48 hours.

In some embodiments, the UFDF is held at a temperature of about 10° C. to about 30° C. In some embodiments, the UFDF is held at a temperature of about 13° C. to about 27° C. In some embodiments, the UFDF is held at a temperature of about 14° C. to about 26° C. In some embodiments, the UFDF is held at a temperature of about 15° C. to about 26° C. In some embodiments, the UFDF is held at a temperature of about 15° C. to about 25° C. In some embodiments, the UFDF is held at a temperature of about 19° C. to about 25° C. In some embodiments, the UFDF is stored at the end of the hold time until further downstream processing steps are performed. In some embodiments, the UFDF is stored at −80° C. after flash freezing.

In some embodiments, the at least one additional purification step further comprises a viral inactivation step. In some embodiments, the viral inactivation step comprises a solvent/detergent viral inactivation process to chemically inactivate viral particles. Exemplary solvent/detergent may comprise 10% Polysorbate 80, 3% TNBP, 50 mM Sodium Phosphate, and 100 mM NaCl.

Chromatography

In some embodiments of the method, the UFDF is subjected to at least one chromatography step to obtain partially purified recombinant alkaline phosphatase. In some embodiments, the UFDF is subjected to at least one chromatography step to obtain partially purified recombinant alkaline phosphatase, wherein the recombinant alkaline phosphatase has a total sialic acid content (TSAC) of about 0.9 mol/mol to about 3.0 mol/mol. In some embodiments, the at least one chromatography step is performed to further purify the product and/or separate the impurities/contaminants. In some embodiments, the at least one chromatography step is protein chromatography. In some embodiments, the protein chromatography is gel filtration chromatography, ion exchange chromatography, reversed-phase chromatography (RP), affinity chromatography, expanded bed adsorption (EBA), mixed-mode chromatography, and/or hydrophobic interaction chromatography (HIC). In some embodiments, the protein chromatography is affinity chromatography. In some embodiments, the protein chromatography is Protein A chromatography. In some embodiments, the Protein A chromatography captures the product (i.e., the alkaline phosphatase, such as asfotase alfa). For example, a process of GE Healthcare Mab Select SuRe Protein A chromatography may be used. Exemplary buffers and solutions used in Protein A chromatography include, e.g., equilibration/wash buffer (e.g., 50 mM Sodium Phosphate, 100 mM NaCl, pH 7.50), elution buffer (e.g., 50 mM Tris, pH 11.0), strip buffer (e.g., 100 mM Sodium Citrate, 300 mM NaCl, pH 3.2), flushing buffer, cleaning solution (e.g., 0.1 M NaOH), etc.

In some embodiments, the at least one chromatography step comprises an additional chromatography and/or purification step. In some embodiments, the at least one additional chromatography step comprises column chromatography. In some embodiments, the column chromatography is gel filtration chromatography, ion exchange chromatography, reversed-phase chromatography (RP), affinity chromatography, expanded bed adsorption (EBA), mixed-mode chromatography, and/or hydrophobic interaction chromatography (HIC). In some embodiments, the column chromatography comprises hydrophobic interaction chromatography (HIC). In some embodiments, the HIC uses Butyl Sepharose or CAPTO® Butyl agarose columns. Exemplary buffers and solutions used in a CAPTO® Butyl agarose HIC process include, e.g., loading dilution buffer/pre-equilibration buffer (e.g., 50 mM sodium phosphate, 1.4 M sodium sulfate, pH 7.50), equilibration buffer/wash buffer/elution buffer (e.g., all containing sodium phosphate and sodium sulfate), strip buffer (e.g., containing sodium phosphate), etc. Exemplary buffers and solutions used in a Butyl HIC process include, e.g., loading dilution buffer/pre-equilibration buffer (e.g., 10 mM HEPES, 2.0 M ammonium sulfate, pH 7.50), equilibration buffer/wash buffer(s)/elution buffer (e.g., all containing sodium phosphate or HEPES and ammonium sulfate), and strip buffer (e.g., containing sodium phosphate).

In some embodiments, the at least one additional purification step comprises an additional diafiltration. In some embodiments, the at least one additional chromatography and/or purification step comprises hydrophobic interaction chromatography and/or at least an additional diafiltration step. In some embodiments, the additional diafiltration step is performed after a hydrophobic interaction chromatography step. In some embodiments, the additional diafiltration step is performed for product concentration and/or buffer exchange. Exemplary buffers and solutions used in this process include, e.g., equilibration buffer (e.g., 20 mM Sodium Phosphate, 100 mM NaCl, pH 6.75), diafiltration buffer (20 mM Sodium Phosphate, 100 mM NaCl, pH 6.75), etc.

In some embodiments, the at least one additional chromatography and/or purification step is performed to obtain recombinant alkaline phosphatase with a TSAC of about 0.5 mol/mol to about 4.0 mol/mol. In some embodiments, the at least one additional chromatography and/or purification step is performed to obtain recombinant alkaline phosphatase with a TSAC of about 0.9 mol/mol to about 3.9 mol/mol. In some embodiments, the at least one additional chromatography and/or purification step is performed to obtain recombinant alkaline phosphatase with a TSAC of about 1.1 mol/mol to about 3.2 mol/mol. In some embodiments, the at least one additional chromatography and/or purification step is performed to obtain recombinant alkaline phosphatase with a TSAC of about 1.4 mol/mol to about 2.6 mol/mol. In some embodiments, the at least one additional chromatography and/or purification step is performed to obtain recombinant alkaline phosphatase with a TSAC of about 1.2 mol/mol to about 3.0 mol/mol. In some embodiments, the at least one additional chromatography step is performed to obtain recombinant alkaline phosphatase with a TSAC of about 0.8 mol/mol, about 0.9 mol/mol, 1.0 mol/mol, about 1.1 mol/mol, about 1.2 mol/mol, about 1.3 mol/mol, about 1.4 mol/mol, about 1.5 mol/mol, about 1.6 mol/mol, about 1.7 mol/mol, about 1.8 mol/mol, about 1.9 mol/mol, about 2.0 mol/mol, about 2.1 mol/mol, about 2.2 mol/mol, about 2.3 mol/mol, about 2.4 mol/mol, about 2.5 mol/mol, about 2.6 mol/mol, about 2.7 mol/mol, about 2.8 mol/mol, about 2.9 mol/mol, about 3.0 mol/mol, about 3.1 mol/mol, about 3.2 mol/mol, about 3.3 mol/mol, about 3.4 mol/mol, about 3.5 mol/mol, about 3.6 mol/mol, about 3.7 mol/mol, about 3.8 mol/mol, about 3.9 mol/mol, or about 4.0 mol/mol.

Additional Downstream Processes

In some embodiments, additional downstream processes are performed in addition to the at least one purification step, the additional purification step, the at least one chromatography step, and/or the additional chromatography step. In some embodiments, the additional downstream processes further purify the product, i.e., the recombinant alkaline phosphatase.

In some embodiments, the additional downstream processes include a viral reduction filtration process to further remove any viral particles. In some embodiments, the viral reduction filtration process is nanofiltration.

In some embodiments, the additional downstream processes include at least one further chromatography step. In some embodiments, the at least one further chromatography step is protein chromatography. In some embodiments, the protein chromatography is gel filtration chromatography, ion exchange chromatography, reversed-phase chromatography (RP), affinity chromatography, expanded bed adsorption (EBA), mixed-mode chromatography, and/or hydrophobic interaction chromatography (HIC). In some embodiments, the third chromatography step is mixed-mode chromatography, such as CAPTO® Adhere agarose chromatography. Commercially available mixed-mode materials include, e.g., resins containing hydrocarbyl amine ligands (e.g., PPA Hypercel and HEA Hypercel from Pall Corporation, Port Washington, NY), which allow binding at neutral or slightly basic pH, by a combination of hydrophobic and electrostatic forces, and elution by electrostatic charge repulsion at low pH (see Brenac et al., 2008 *J Chromatogr A*. 1177:226-233); resins containing 4-mercapto-ethyl-pyridine ligand (MEP Hypercel, Pall Corporation), which achieves hydrophobic interaction by an aromatic residue and the sulfur atom facilitates binding of the target protein by thiophilic interaction (Lees et al., 2009 *Bioprocess Int*. 7:42-48); resins such as CAPTO® MMC mixed-mode chromatography and CAPTO® adhere agarose chromatography (GE Healthcare, Amersham, UK) containing ligands with hydrogen bonding groups and aromatic residues in the proximity of ionic groups, which leads to the salt-tolerant adsorption of proteins at different conductivities (Chen et al., 2010 *J Chromatogr A*. 1217:216-224); and other known chromatography materials, such as affinity resins with dye ligands, hydroxyapatite, and some ion-exchange resins (including, but not limited to, Amberlite CG 50 (Rohm & Haas, Philadelphia, PA) or Lewatit CNP 105 (Lanxess, Cologne, DE). For an exemplary agarose HIC chromatography step, exemplary buffers and solutions used in this process include, e.g., pre-equilibration buffer (e.g., 0.5 M Sodium Phosphate, pH 6.00), equilibration/wash buffer (e.g., 20 mM Sodium Phosphate, 440 mM NaCl, pH 6.50), load titration buffer (e.g., 20 mM Sodium Phosphate, 3.2 M NaCl, pH 5.75), pool dilution buffer (e.g., 25 mM Sodium Phosphate, 150 mM NaCl, pH 7.40), and strip buffer (0.1 M Sodium Citrate, pH 3.20.

In some embodiments, the additional downstream processes comprise a virus filtration step for viral clearance. In some embodiments, the viral filtration step is performed by size exclusion chromatography. Exemplary buffers and solutions used in this process include, e.g., pre-use and post-product flush buffer (e.g., 20 mM Sodium Phosphate, 100 mM NaCl, pH 6.75).

In some embodiments, the additional downstream processes comprise a formulation process. In some embodiments, the formulation process comprises at least one further ultrafiltration and/or diafiltration for further concentration and/or buffer exchange. Exemplary buffers and solutions used in this process include, e.g., filter flush/equilibration/diafiltration/recovery buffer (e.g., 25 mM Sodium Phosphate, 150 mM NaCl, pH 7.40).

In some embodiments, the additional downstream processes comprise a bulk fill process. In some embodiments, the bulk fill process comprises sterile filtration. Exemplary filters for sterile filtration are Millipak 60 or Equivalent sized PVDF filters (EMD Millipore, Billerica, MA.

In some embodiments, the steps used for producing, purifying, and/or separating the alkaline phosphatase from the culture cells, as disclosed herein, further comprise at least one of steps selected from the group consisting of: a harvest clarification process (or a similar process to remove the intact cells and cell debris from the cell culture), an ultrafiltration (UF) process (or a similar process to concentrate the produced alkaline phosphatase), a diafiltration (DF) process (or a similar process to change or dilute the buffer comprising the produced alkaline phosphatase from previous processes), a viral inactivation process (or a similar process to inactivate or remove viral particles), an affinity capture process (or any one of chromatography methods to capture the produced alkaline phosphatase and separate it from the rest of the buffer/solution components), a formulation process and a bulk fill process. In one embodiment, the steps for producing, purifying, and/or separating the alkaline phosphatase from the culture cells, as disclosed herein, comprise at least a harvest clarification process (or a similar process to remove the intact cells and cell debris from the cell culture), a post-harvest ultrafiltration (UF) process (or a similar process to concentrate the produced alkaline phosphatase), a post-harvest diafiltration (DF) process (or a similar process to change or dilute the buffer comprising the produced alkaline phosphatase from previous processes), a solvent/detergent viral inactivation process (or a similar process to chemically inactivate viral particles an intermediate purification process (such as hydrophobic interaction chromatography (HIC) or any one of chromatography methods to capture the produced alkaline phosphatase and separate it from the rest of the buffer/solution components), a post-HIC UF/DF process (or a similar process to concentrate and/or buffer exchange for the produced alkaline phosphatase), a viral reduction filtration process (or a similar process to further remove any viral particles or other impurities or contaminants); a mixed-mode chromatography (such as CAPTO® Adhere agarose chromatography, or a similar process to further purify and/or concentrate the produced alkaline phosphatase), a formulation process and a bulk fill process. In one embodiment, the separating step of the method provided herein further comprises at least one of harvest clarification, ultrafiltration, diafiltration, viral inactivation, affinity capture, HIC chromatography, mixed-mode chromatography and combinations thereof. FIG. 1 is an exemplary illustration of an embodiment of the production process of a recombinant alkaline phosphatase, asfotase alfa.

In some embodiments, the disclosure provides a method for controlling total sialic acid content (TSAC) in a TSAC-containing recombinant protein through mammalian cell culture, comprising at least one purification step and at least one chromatography step. In some embodiments, the disclosure provides a method for controlling glycosidase activity in mammalian cell culture producing recombinant protein, comprising at least one purification step and at least one chromatography step. In some embodiments, the at least one purification step comprises at least one of filtration, centrifugation, harvest clarification, filtration, ultrafiltration, diafiltration, viral inactivation, affinity capture, and combinations thereof. In some embodiments, the at least one chromatography step comprises protein chromatography. In some embodiments, the protein chromatography is gel filtration chromatography, ion exchange chromatography, reversed-phase chromatography (RP), affinity chromatography, expanded bed adsorption (EBA), mixed-mode chromatography, and/or hydrophobic interaction chromatography (HIC). In some embodiments, the purification step and chromatography step are ultrafiltration/diafiltration and protein A chromatography.

All references cited herein are incorporated by reference in their entirety. Although the foregoing disclosure has been described in some detail by way of illustration and example for purposes of clarity of understanding, it is apparent to those skilled in the art that certain minor changes and modifications will be practiced. Therefore, the description and examples should not be construed as limiting the scope of the disclosure.

EXAMPLES

Example 1: Production of Asfotase Alfa and TSAC Measurement

Asfotase alfa (or other glycoprotein of interest) is manufactured by known methods. In particular, inoculum expansion is performed from the appropriate recombinant cell line (i.e., transfected CHO cells carrying GS resistance marker, selected in the presence of MSX), which is sample aliquoted into the appropriate growth media, then further grown in a bioreactor at controlled temperature, pH, $DO_2$, and agitation. Typical production methods for asfotase alfa are fed-batch bioreactor methods with CHO cells, though other methods are also acceptable. When a desired cell density and/or cell viability has been reached, the primary recovery from the raw Cell Culture Fluid (CCF) is performed by centrifugation and depth filtration which results in the Harvest Cell Culture Fluid (HCCF).

The HCCF is further purified by ultrafiltration and diafiltration to form the UFDF. Further chromatographic purification steps are performed, such as viral inactivation, protein A chromatography (resulting in a protein A pool), multimodal chromatography purification, and additional ultrafiltration and diafiltration steps. The final bulk drug substance, or purified recombinant asfotase alfa, is tested for release specifications. The bulk drug substance proceeds to final fill finish steps, which result in final packaging suitable for administration.

During manufacturing, the TSAC content is an important value and is monitored closely. However, the specific impact of hold time and temperature on TSAC was not fully understood. Therefore, identification and quantitation of sialic acid in asfotase alfa samples at various stages of manufacture was performed by high performance anion exchange chromatography with pulsed amperometric detection (HPAE-PAD). (Commercial systems for carbohydrate detection and quantitation are available, i.e., ThermoScientific and others.) Samples were first spiked with internal standard and dried in a rotary evaporator and sialic acids were released via acid hydrolysis (0.1M HCl). Samples were dried again to remove residual acid then reconstituted in water to be injected into a capillary ion chromatography system (Dionex IC-5000). After injection, samples undergo anion exchange chromatography in an alkaline environment using an acetate gradient for separation of sialic acid species, from 5% acetate buffer to 30% acetate buffer over 30 minutes with a 5 minute equilibration at 5% acetate buffer at the end of each injection. Separation occurs in an HPLC column designed for carbohydrate separation (i.e., CarboPac PA100 column, where a stationary phase of nonporous beads coated with latex in conjunction with alkaline mobile phases separates based on charge). Post separation, samples were detected via pulsed amperometric detection. A repeating waveform oxidized samples at the surface of a gold electrode, where the difference of electrical potential between oxidized sample and the gold electrode is measured. Results are plotted as electrical potential (nC) vs time and peaks are integrated. Percent of internal standard (% ISTD) is calculated via Neu5Ac or Neu5Gc peak area divided by the internal standard, 3-deoxy-D-glycero-D-galacto-2-nonulosonic acid (KDN, Sigma-Aldrich), area multiplied by 100, and quantitated by comparison to a standard curve of standard % ISTD vs standard concentration. Sample concentration is determined by interpolating sample % ISTD from the standard curve. A blend of Neu5Ac and Neu5Gc sialic acids was used as an assay standard, allowing the method to quantitate both species. Results are reported in nmol Neu5Ac per nmol monomer. Neu5Gc is not expected to be present in amounts above the LOQ of the assay; however samples exhibiting quantifiable Neu5Gc are noted in routine experimentation.

The mole ratio of sialic acid to protein for each sample is calculated by dividing the nmol amount of sialic acid recovered by the nmol amount of protein (i.e., asfotase alfa) hydrolyzed by using the concentration (as determined by absorbance of the sample at 280 nm and adjusted by the molar extinction coefficient and the molecular weight).

Additional details on the some embodiments of the methods of the production of asfotase alfa can be found in International Publications WO 2017/031114 and WO 2017/214130, the disclosures of which are hereby incorporated by reference in their entireties.

Example 2: Evaluation of UFDF Hold Time, Temperature, and Protein Concentration on TSAC During large-scale production of asfotase alfa (as described generally in Example 1), a drop in TSAC from harvested cell culture fluid (HCCF) to Protein A pool was observed. This difference was expected to be largely due to the post-harvest concentration/diafiltration (UF/DF1) hold step. The average decrease in TSAC observed from HCCF to protein A pool was approximately 1.1 mol/mol with a standard deviation of 0.2 mol/mol, with a range of 0.9 mol/mol to 1.3 mol/mol.

Figure 2:
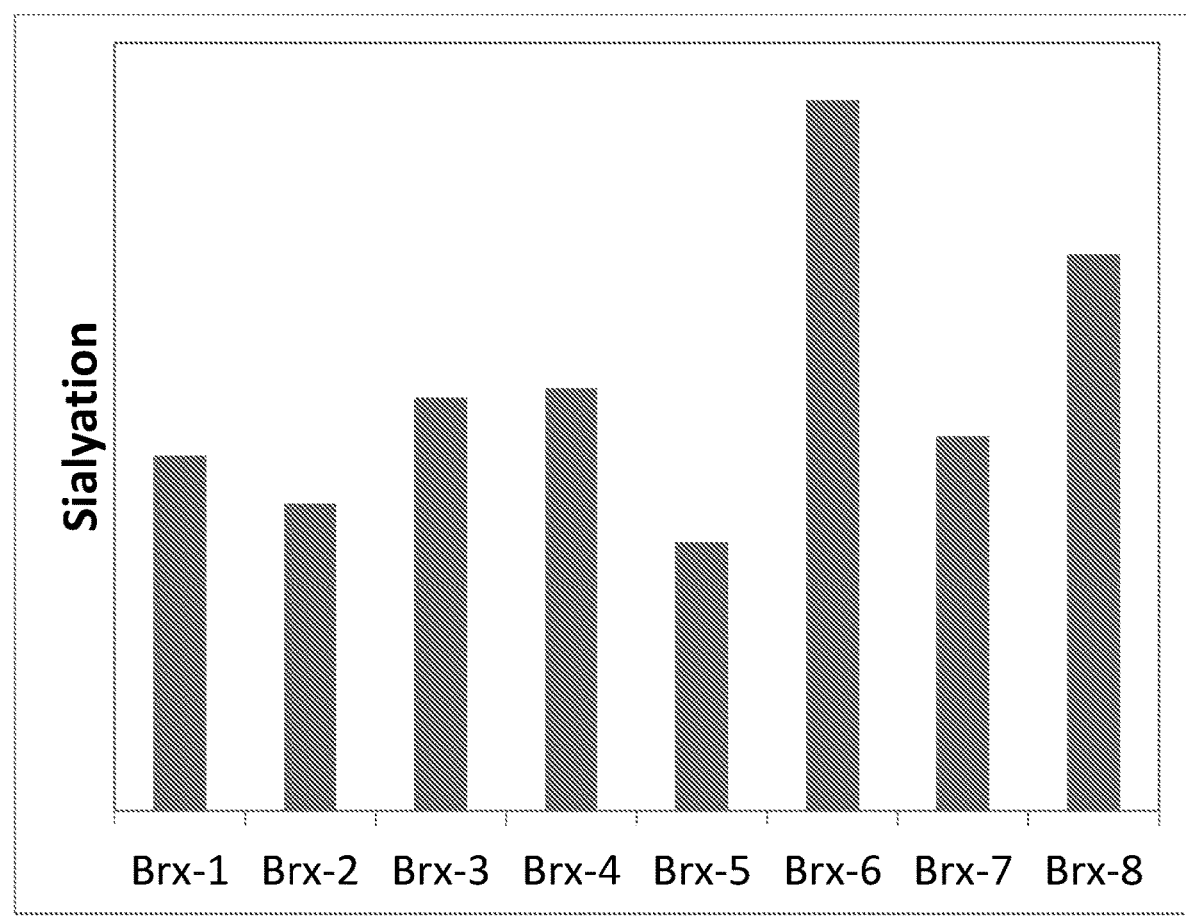
FIG. 2 represents protein siaylation of cells grown with the addition of various nutrient supplements, and with and without a temperature shift. Brx-1=Control Process with temperature shift; Brx-2=Control Process with temperature shift; Brx-3=Cell Boost 2+5 with temperature shift; Brx-4=Cell Boost 2+5 with temperature shift; Brx 5=Cell Boost 6 with temperature shift; Brx-6=Cell Boost 6 without temperature shift; Brx-7=Cell Boost 7a+7b with temperature shift; Brx-8=Cell Boost 7a+7b without temperature shift. Day 14 values shown.

FIG. 2 illustrates the relative protein sialyation of cells grown with the addition of various nutrient supplements for 14 days, and with and without a temperature shift of about 37° C. to about 30° C. when the culture reaches a cell density of at least about $2.5 \times 10^6$ viable cells. Brx-1=Control Process with temperature shift; Brx-2=Control Process with temperature shift; Brx-3=Cell Boost 2+5 with temperature shift; Brx-4=Cell Boost 2+5 with temperature shift; Brx 5=Cell Boost 6 with temperature shift; Brx-6=Cell Boost 6 without temperature shift; Brx-7=Cell Boost 7a+7b with temperature shift; Brx-8=Cell Boost 7a+7b without temperature shift.

Figure 3A:
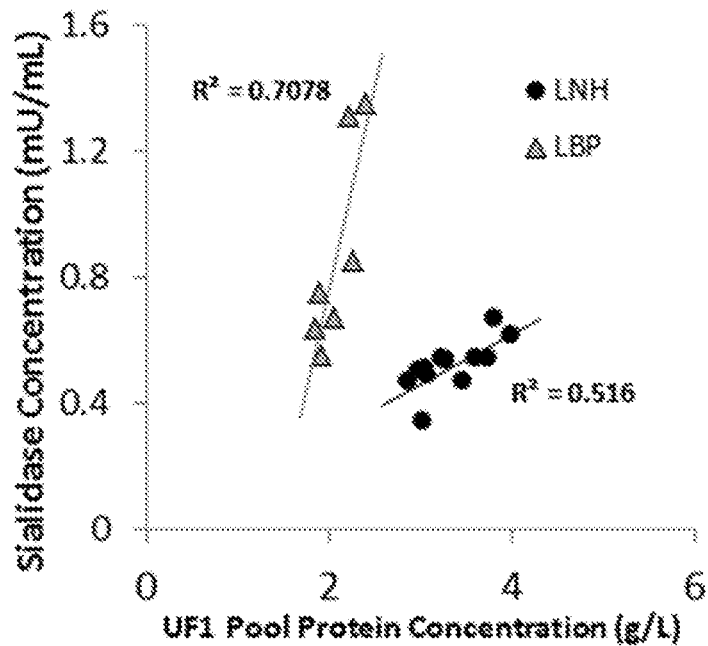
FIG. 3A and FIG. 3B represent the correlation between TSAC decline and protein concentration (FIG. 3A) and temperature (FIG. 3B) during the HCCF post-harvest concentration/diafiltration (UF/DF) hold.
Figure 3B:
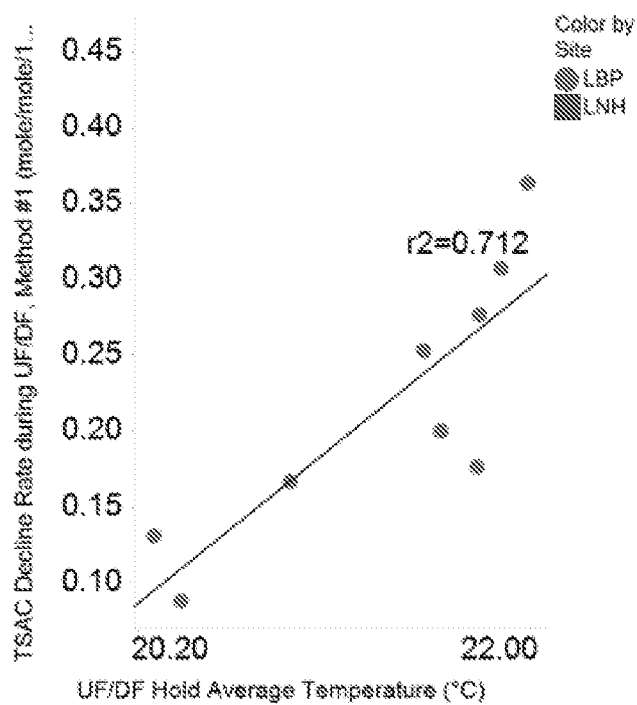

FIG. 3 illustrates the correlation between TSAC decline and protein concentration (Panel A) and hold temperature (Panel B).

A small-scale characterization study was executed to assess and characterize the impact of UF/DF1 hold time, temperature, and protein concentration on TSAC during the UF/DF1 hold.

Example 2.1: UF/DF1 Operation and Hold

Figure 4:
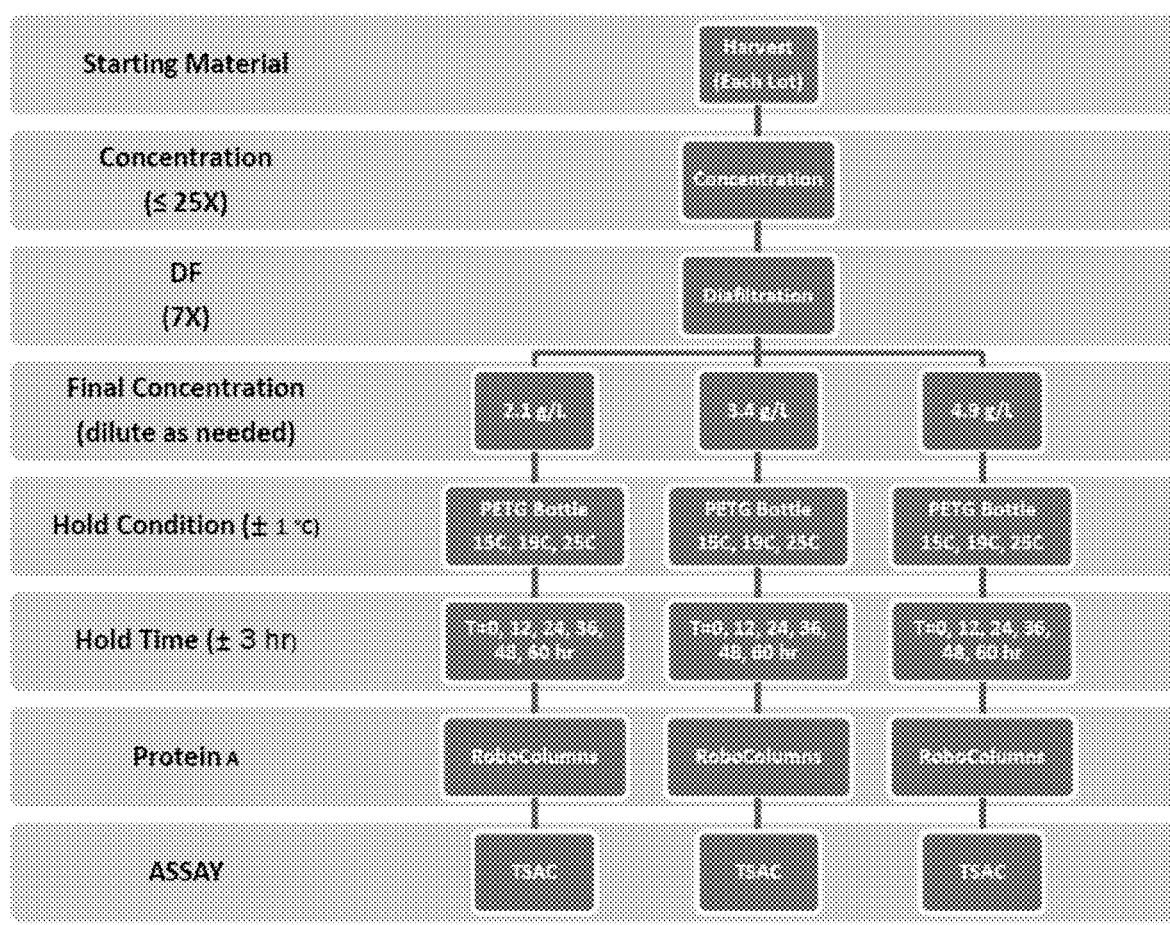
FIG. 4 is an overview of the small-scale UF/DF1 operation and hold time performed for each of three 10 L clarified harvest lots, as described in Example 2.

FIG. 4 outlines the small-scale UF/DF1 operation and hold time performed for each of three 10 L clarified harvest lots. Table 1 and Table 2 list the target process conditions and process parameters for the post-harvest UF/DF1 step.

TABLE 1

UF/DF1 Process Conditions

| Process Parameter | Target |
|---|---|
| TFF membrane used | Millipore Biomax C screen |
| Membrane cutoff (Da) | 50,000 |
| TMP | 15 PSI (10-20 PSI target range; 22 PSI maximum) |
| Cross flow rate | 6-8 L/m$^2$/min |
| Filter area (m$^2$) | 0.1 |
| Filter load (L/m$^2$) | ≤250 |

TABLE 2

Post Harvest Concentration/Diafiltration (UF/DF1)

| Step | Buffer | Volume | Cross Flow Rate |
|---|---|---|---|
| WFI Rinse | WFI | 5 L/m$^2$ | 8 L/m$^2$/min |
| Pre-use Clean | 0.5M NaOH | 5 L/m$^2$ | 8 L/m$^2$/min |
| WFI Rinse | WFI | 5 L/m$^2$ | 8 L/m$^2$/min |
| NWP | 0.1M NaOH | N/A | 5 L/m$^2$/min |
| Equilibration | 50 mM Sodium Phosphate 100 mM Sodium Chloride pH 7.5 | 5 L/m$^2$ | 8 L/m$^2$/min |
| Concentration | Harvest | 25X maximum | 6 L/m$^2$/min |
| Diafiltration | 50 mM Sodium Phosphate 100 mM Sodium Chloride pH 7.5 | 7X | 6 L/m$^2$/min |
| Product Recovery | 50 mM Sodium Phosphate 100 mM Sodium Chloride pH 7.5 | Chase/concentrate as needed to target 4.9 mg/mL and dilute aliquots immediately to target final concentrations.[1] | 4 L/m$^2$/min |
| WFI Rinse | WFI | 20 L/m$^2$ | 5 L/m$^2$/min |
| Clean | 0.5M NaOH, 400 ppm bleach | 5 L/m$^2$ | 8 L/m$^2$/min |
| WFI Rinse | WFI | 5 L/m$^2$ | 8 L/m$^2$/min |
| Store | 0.2M NaOH | 5 L/m$^2$ | 8 L/m$^2$/min |

[1]Generating samples at high concentration required a final concentration factor above the transferred range (≤25X) and was governed by harvest titer. To achieve the higher concentration, a final concentration step (UF1') was performed prior to product recovery.

In-process samples at the end of UF1 and end of DF were pulled for purification and TSAC analysis. Generating samples at high concentration required a final concentration step (UF1') that resulted in a concentration factor above the transferred range (≤25 X) and was governed by the estimated harvest titer of each individual lot. The lower concentrations were achieved by dilution with DF buffer Immediately following completion of the UF/DF1, the pool was diluted according to the study design (FIG. 4) and divided into aliquots and used for the hold study. The UF/DF1 pool was then split into 15 mL conical tubes and held at the specific target temperatures ±1° C. (15, 19, or 25° C.) in controlled water baths for 0, 12, 24, 36, 48, and 60 hours before further processing. All holds were executed ±2 hours of hold target and once timepoints were reached, aliquots were frozen (−80° C.) until Protein A purification.

T=0 in this study was defined as the time at which a 10 minute recirculation was completed at the end of the diafiltration (DF) step. During manufacturing operations, the start of the hold time is currently defined as the end of bag fill following UF/DF1 product filtration and transfer. The transfer takes approximately 5 hours on average from the end of diafiltration, which is in addition to the hold time for the UF/DF1 pool.

Example 2.2: High Throughput MabSelect SuRe Protein a Chromatography

UF/DF1 hold samples were processed through MabSelect SuRe pre packed RoboColumns without the solvent/detergent viral inactivation (S/D VI) step. Removal of the S/D VI step does not affect TSAC results and improves processing time for the high throughput RoboColumn method (DVL 16 0128). Table 3 presents the MabSelect SuRe RoboColumn affinity chromatography step. The operation was performed using pre-packed MabSelect SuRe RoboColumns and the Tecan Freedom Evo Liquid Handling system. Samples were purified in batches with up to 8 samples per batch. Prior to purification of each sample batch, samples were thawed in a water bath (18-25° C.) for ≤1 hour.

The elution from each RoboColumn purification was collected across four 96-well plates (approximately 200 μl per well) and the absorbance (A280) measured for each well. For each column, elution wells containing product were pooled via micropipetting on the basis of the collection criteria defined in Table 3 and pools were sterile filtered (0.22 μm). The ProA pools were not pH adjusted or diluted.

TABLE 3

MabSelect SuRe RoboColumn Chromatography

| Step | Buffer | CV | Flow Rate (cm/hr) |
|---|---|---|---|
| Clean | 0.1M Sodium Hydroxide | 5 | 150 |
| Equilibration | 50 mM Sodium Phosphate 100 mM Sodium Chloride pH 7.5 | 8 | 150 |
| Load | UF/DF1 Retentate | | 100 |
| Post Load Wash 1 | 50 mM Sodium Phosphate 100 mM Sodium Chloride pH 7.5 | 3.5 | 150 |
| Elution | 50 mM Tris pH 11.0 | 16 | 100 |
| Strip | 100 mM Sodium Citrate 300 mM Sodium Chloride pH 3.2 | 5.5 | 150 |
| WFI Flush | WFI | 3 | 150 |
| Clean | 0.1M Sodium Hydroxide | 5 | 150 |
| Equilibration | 50 mM Sodium Phosphate 100 mM Sodium Chloride pH 7.5 | 3 | 150 |
| Store | 18% Ethanol | 3 | 100 |

Example 2.3: Results—TSAC at HCCF/in-Process Samples

Table 4 lists the UF/DF1 in-process TSAC data generated across all three harvest lots. There is a drop in TSAC expected from HCCF to the start of the UF/DF1 hold (T=0)

due to the higher concentrations of both product and sialidase that are achieved in the UF1 step and then maintained throughout the remainder of the UF/DF1 operation. However, this TSAC decrease is only expected to be a small fraction of the total TSAC drop from HCCF to Protein A given the processing time is minimal relative to the total UF/DF1 pool hold time. To assess this decrease, TSAC results from all T=0 samples for each harvest UF/DF1 batch were averaged and then subtracted from the starting TSAC at HCCF of the batch. Given the duration from end of UF/DF1 operation and T=0 sampling (diluted and frozen within 2 hours of hold start time), minimal variability (within ±10% assay variability) is expected across the T=0 samples despite the varying protein concentrations. Therefore, averaging the results from the T=0 samples provides more confidence in the T=0 result and minimizes the impact of assay variability.

As shown in Table 4, the reported TSAC at HCCF for harvest batch #B is 3.6 mol/mol and the average TSAC result for the T=0 samples is 2.5 mol/mol. A 0.9 mol/mol drop in TSAC is therefore calculated during the UF/DF1 operation for this lot. This extent of TSAC drop is more typically seen after the UF/DF1 hold (14-48 hrs) has been completed, suggesting one of the TSAC results for this lot may have been an outlier. The additional small scale in process results for batch #B provided evidence that the TSAC value for HCCF was the outlier assay result since the averaged TSAC at T=0 aligned well with the UF/DF1 in process results (End UF1, End DF) shown below. Additionally, the TSAC value measured for CCF of this manufacturing batch is 2.7 mol/mol and the difference between the TSAC results at CCF and HCCF for this batch was inconsistent with process expectations.

TABLE 4

HCCF and UF/DF1 In-process sample TSAC Data summary

| Harvest Lot # | A | B | C |
|---|---|---|---|
| | TSAC (mol/mol) | | |
| HCCF | 3.4 | 3.6 | 2.9 |
| End UF1 | 3.3 | 2.4 | 2.7 |
| End DF | 3.1 | 2.2 | 2.7 |
| End of UF1' (T = 0, average) | 3.0 | 2.7[1] | 2.4 |
| Drop from HCCF to end of UF/DF1 process[2] | 0.4 | 0.9 | 0.5 |

[1]Average of only two TSAC values (excluded low concentration sample as it will not be included in final analysis)
[2]Calculation: TSAC at HCCF − TSAC at End of UF1' (T = 0)

An accurate TSAC at HCCF result is required to analyze the TSAC drop from HCCF to the Protein A pool (TSAC drop=TSAC at HCCF−TSAC at ProA Pool). To minimize the impact of a potentially aberrant result for TSAC at HCCF for harvest batch #B on subsequent analyses, an average TSAC value was calculated using in process results from HCCF through T=0. Included in the average is the original TSAC at HCCF result of 3.6 mol/mol, the TSAC at end of UF1 (2.4 mol/mol), the TSAC at end of DF (2.2 mol/mol), and the TSAC values at T=0. In this case, only two of the three T=0 values were used in this calculation, since the result from the lowest hold temperature and lowest UF/DF1 protein concentration was ultimately excluded from the data set (see FIG. 5). As shown in Table 5, an averaged TSAC at HCCF value of 2.7 mol/mol will be used in the small scale characterization data analysis for harvest batch #B. The assumption that 2.7 mol/mol is an appropriate estimate of TSAC at HCCF for this lot will be assessed as part of the statistical analysis and validation of the predictive model.

TABLE 5

Revised HCCF and UF/DF1 In-process sample TSAC Data summary

| | Harvest Lot # | A | B | C |
|---|---|---|---|---|
| TSAC (mol/mol) | HCCF | 3.4 | 2.7[1] | 2.9 |
| | End UF1 | 3.3 | 2.4 | 2.7 |
| | End DF | 3.1 | 2.2 | 2.7 |
| | End of UF1' (T = 0, average) | 3.0 | 2.7[2] | 2.4 |
| | Drop from HCCF at end of UF/DF1 process[3] | 0.4 | 0.0 | 0.5 |

[1]"Harvest" value = average of QC result, end UF, end DF, and both T = 0 samples
[2]Average of only two TSAC values (excluded low concentration sample as it will not be included in final analysis)
[3]Calculation: TSAC at HCCF − TSAC at End of UF1' (T = 0)

Example 2.4: TSAC at Protein A

Figure 5:
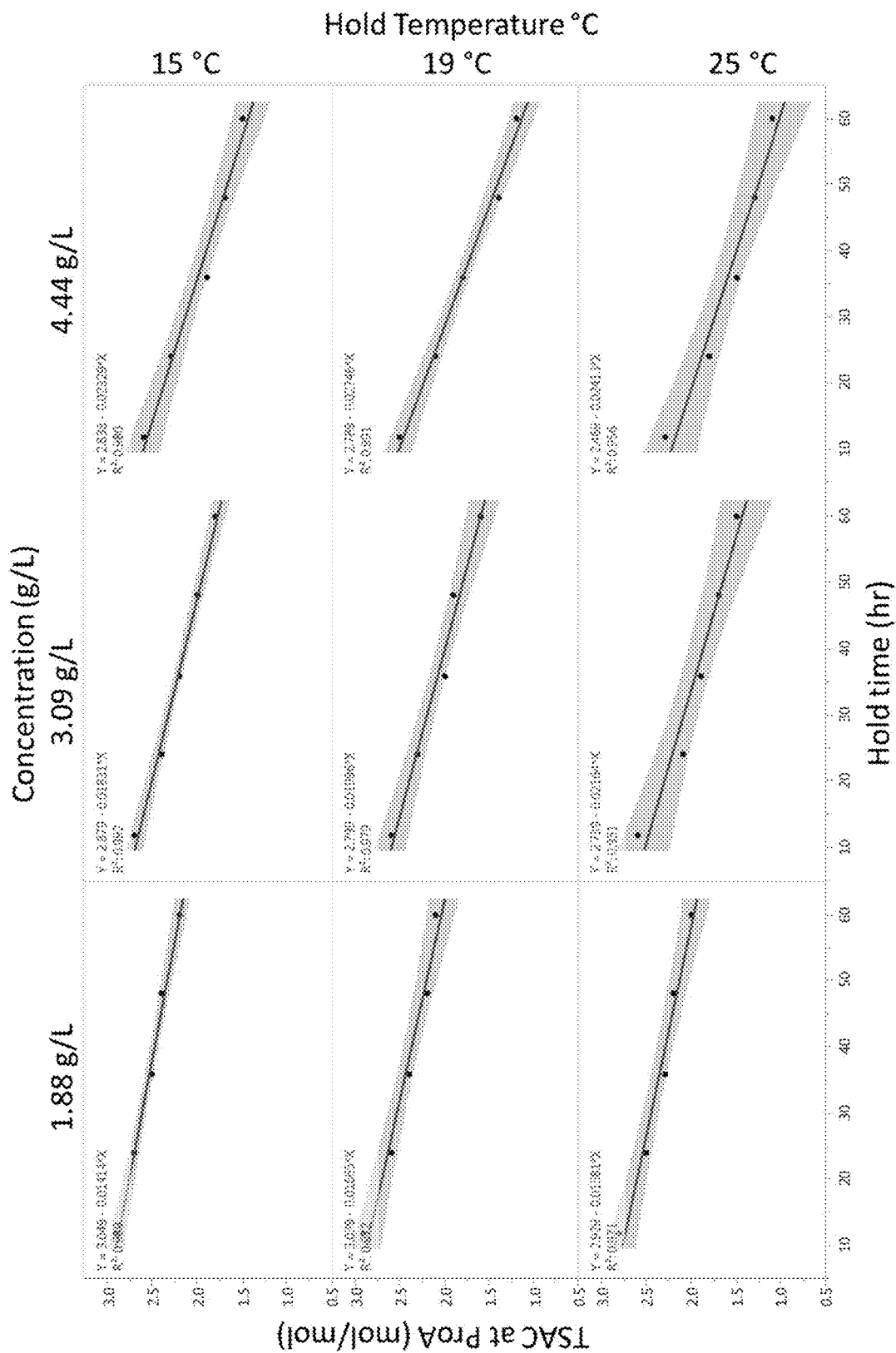
FIG. 5 represents the TSAC versus hold time, temperature, and protein concentration at the Protein A chromatography pool step for harvest batch #A. Three protein concentrations (1.88 g/L, 3.09 g/L, and 4.44 g/L); three hold temperatures (15° C., 19° C., and 25° C.); and five hold times (12, 24, 36, 48, and 60 hours) were tested.
Figure 6:
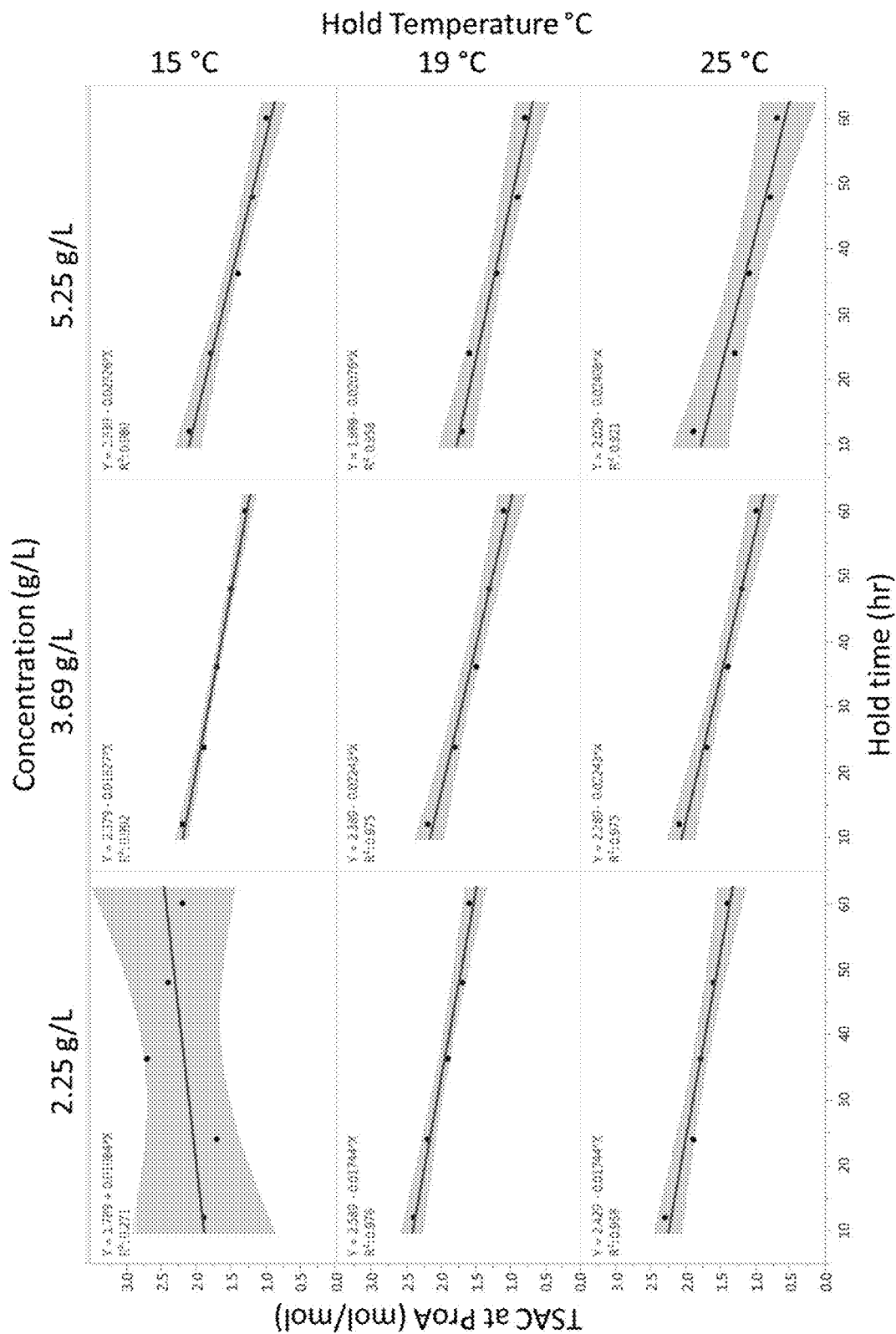
FIG. 6 represents the TSAC versus hold time, temperature, and protein concentration at the Protein A chromatography pool step for harvest batch #B. Three protein concentrations (2.25 g/L, 3.69 g/L, and 5.25 g/L); three hold temperatures (15° C., 19° C., and 25° C.); and five hold times (12, 24, 36, 48, and 60 hours) were tested.
Figure 7:
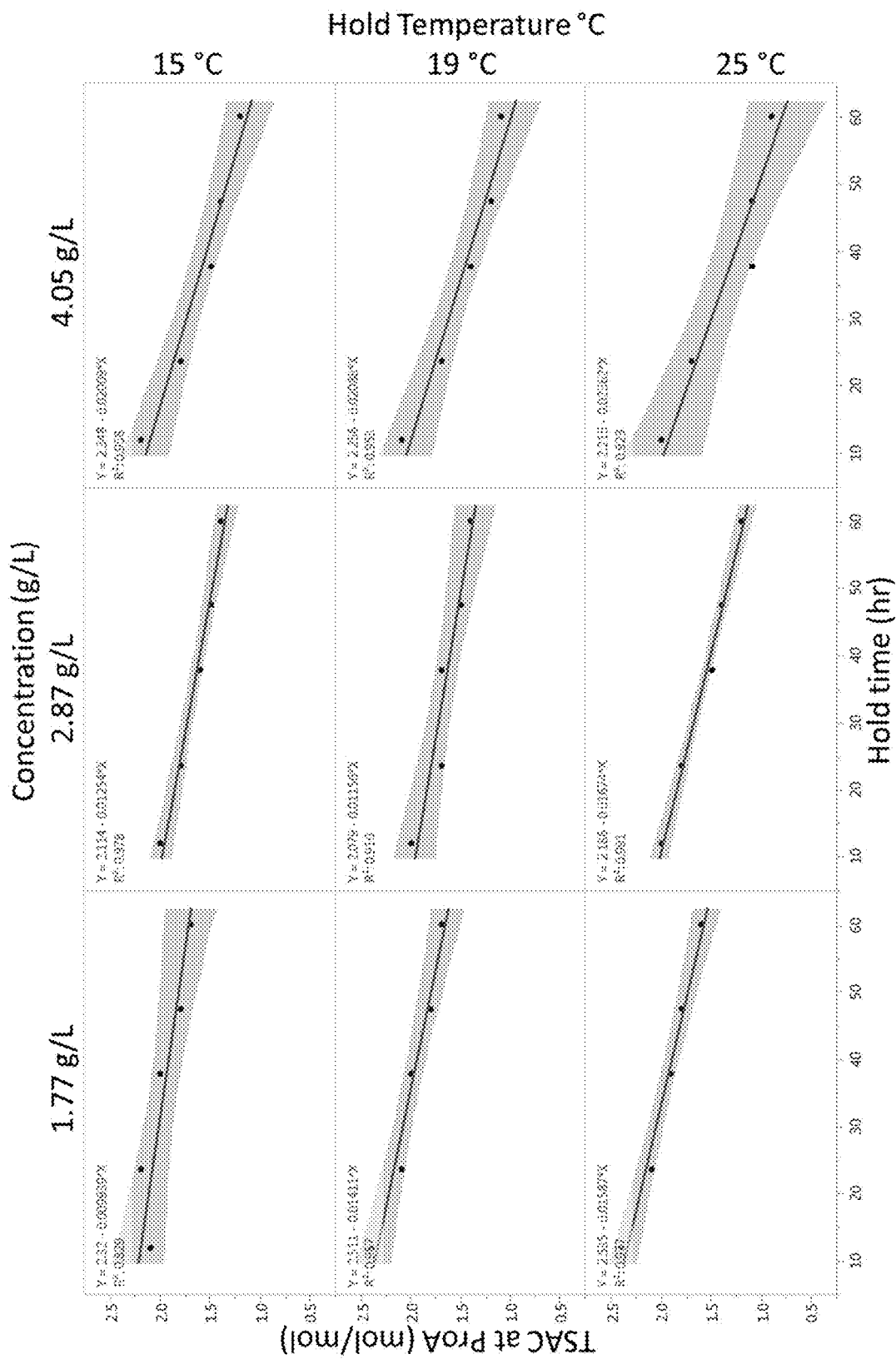
FIG. 7 represents the TSAC versus hold time, temperature, and protein concentration at the Protein A chromatography pool step for harvest batch # C. Three protein concentrations (1.77 g/L, 2.87 g/L, and 4.05 g/L); three hold temperatures (15° C., 19° C., and 25° C.); and five hold times (12, 24, 36, 48, and 60 hours) were tested.

FIG. 5 through FIG. 7 plot the data to show the TSAC decline during the UF/DF1 hold at the various protein concentrations and hold temperatures, starting at the T=12 timepoint samples. Overall, the combined dataset confirms the expected linear drop during the UF/DF1 hold time. There is also a consistent increase in the slope of the TSAC decline with increasing protein concentration of the UF/DF1 pool. However, there is no clear trend between TSAC drop and the UF/DF1 hold temperature. Similar trends in TSAC drop are observed across all three datasets indicating consistent TSAC behavior for the three harvest lots used in this study.

Example 3: TSAC Measurement after Protein A Chromatography and Bulk Fill

Figure 8:
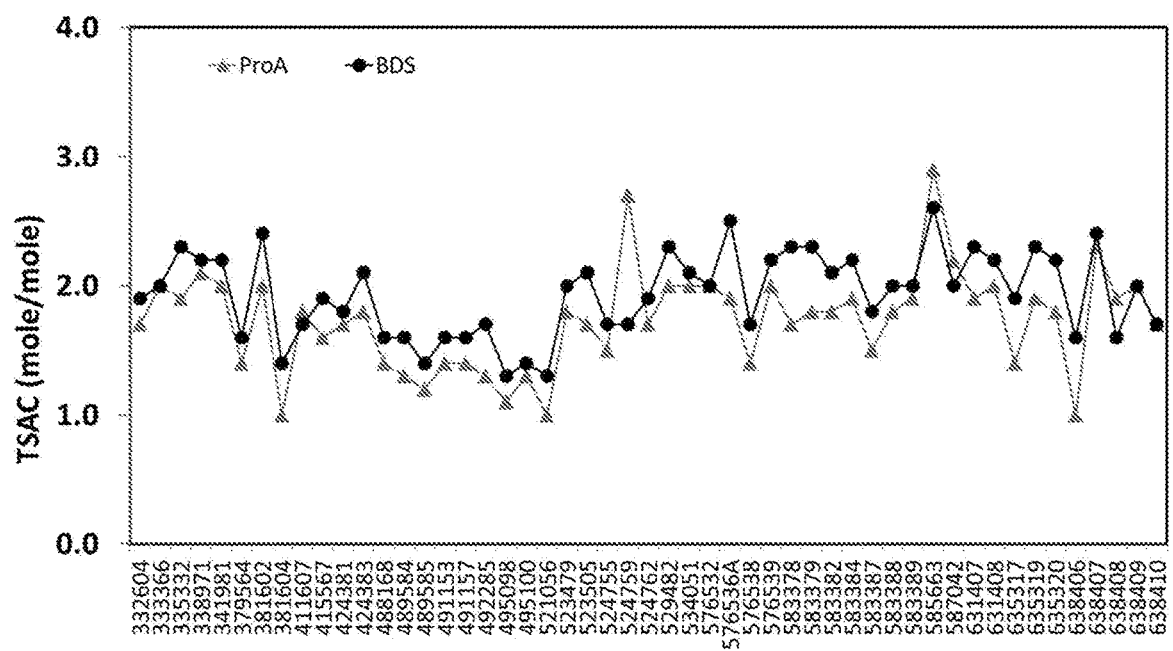
FIG. 8 shows the TSAC measurement after the Protein A chromatography step (ProA) and at the bulk drug substance fill step (BDS) for 51 manufacturing batches.

Total sialic acid content (TSAC) was measured at two steps of the manufacturing process for asfotase alfa: after Protein A Chromatography (also referred to as the Protein A or ProA pool) and Bulk Fill (also referred to as the bulk drug substance or BDS release) (see FIG. 1). The TSAC data from the ProA pool and the BDS release were reviewed for 51 manufacturing batches, as shown in FIG. 8. The BDS TSAC results range from 1.3 to 2.6 mol/mol with a mean 1.9 mol/mol and standard deviation of 0.3 mol/mol (RSD=17.5%). As shown in FIG. 8, the BDS TSAC data and the ProA TSAC data trend closely for each batch, except for batch #524759. The data from this example indicate that unit operations downstream of the Protein A pool step do not significantly contribute to TSAC variability.

Example 4: TSAC Measurement Before and After Harvest

Figure 9:
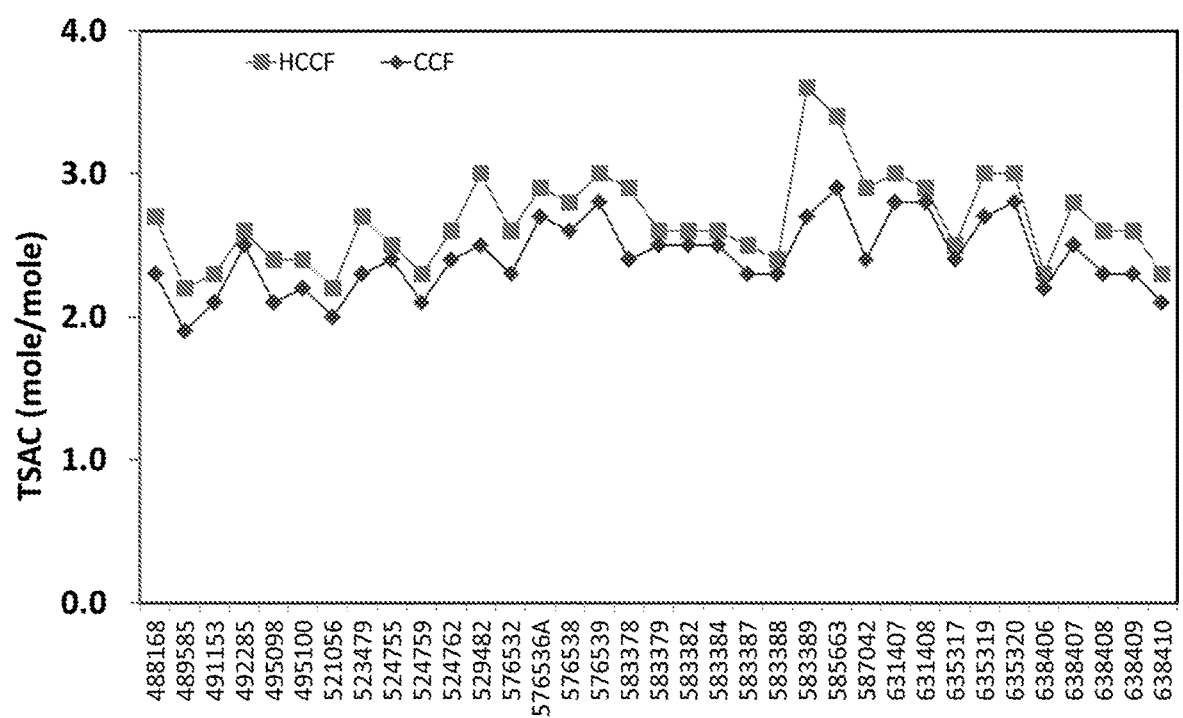
FIG. 9 shows the TSAC measurement at the cell culture fluid (CCF) and the harvest clarified culture fluid (HCCF) for 39 manufacturing batches.

Total sialic acid content (TSAC) was measured in the cell culture fluid (CCF) and harvest clarified culture fluid (HCCF) (see FIG. 1). The TSAC data from the CCF was measured for 39 manufacturing batches, as shown in FIG. 9. The CCF samples were taken at the end of the Production Bioreactor run and were filtered to remove cells and cellular debris, and then stored at appropriate conditions prior to small scale Protein A purification and TSAC analysis. The measured results of TSAC at the CCF range from 1.9 to 2.9 mol/mol with a mean 2.4 mol/mol and standard deviation of 0.3 mol/mol (RSD=10.4%). TSAC data at harvest (HCCF) was measured for 35 of the 39 batches. The HCCF TSAC results ranged from 2.2 to 3.4 mol/mol with a mean of 2.7 mol/mol and standard deviation of 0.3 mol/mol (RSD=10.7%). As shown in FIG. 9, for batches where data are available at both the CCF and HCCF, the HCCF TSAC trends similarly with the CCF TSAC, with approximately a 0.2 mol/mol increase on average (with the exception of batch #B). The ProA and BDS TSAC results for this batch align with the CCF TSAC result, and the HCCF result is considered an outlier. The data from this example indicate that the harvest process does not add variability to TSAC.

Additional multivariate analysis performed on cell culture fluid did not identify a statistically significant impact from cell generation number (32 to 51 generations) at the inoculation of production bioreactor on CCF TSAC (data not shown). A subsequent analysis confirmed no statistically significant correlation between generation number with the tested ranged and TSAC at CCF or HCCF.

Example 5: TSAC Measurement Before and after Harvest

Figure 10:
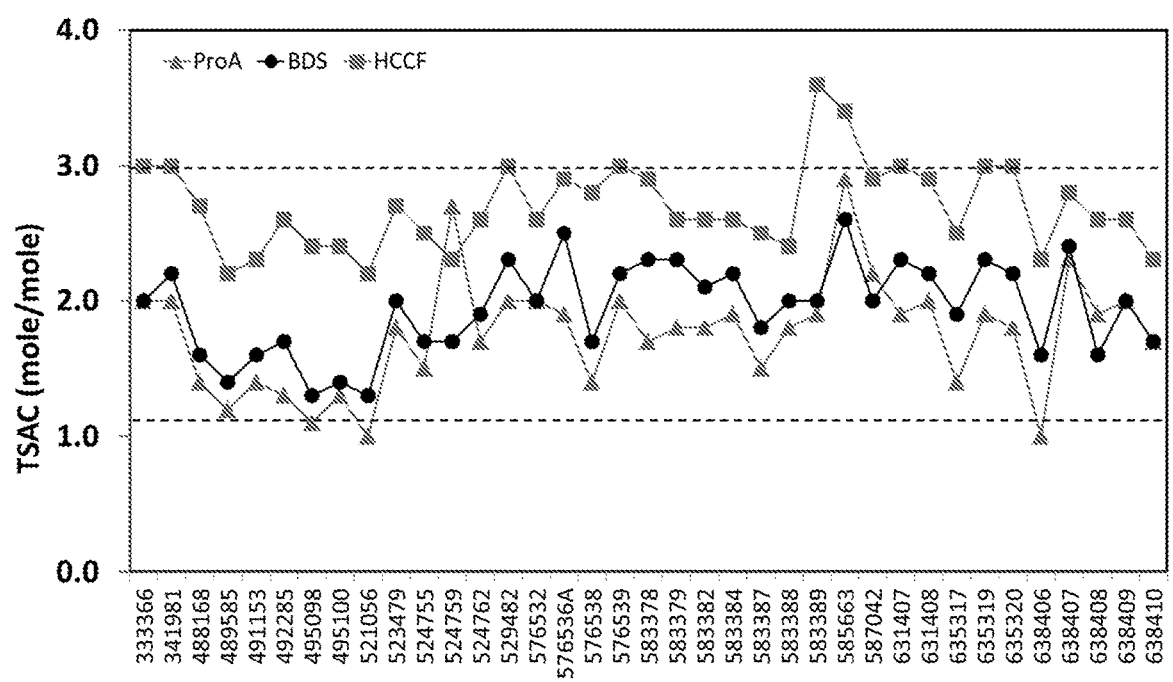
FIG. 10 shows the TSAC measurement at the harvest clarified culture fluid, (HCCF), the Protein A chromatography step (ProA), and the bulk drug substance fill step (BDS) for 39 manufacturing batches.

A review of TSAC measurement collected at various points in the manufacturing process shows that the decrease in TSAC between the HCCF and Protein A pool occurs over the hold after UF/DF1 (also known as the UF1 hold; see FIG. 1). As shown in FIG. 10, TSAC decreases significantly during the UF1 hold for all batches except for batch #583389, which specific data point was excluded as an outlier. The corresponding BDS result for this batch confirms that a decrease in TSAC result similar to the other batches was observed during UF1 hold for this batch. The average decrease in TSAC result over the duration of the UF1 hold was approximately 1.0 mol/mol with a standard deviation of 0.3 mol/mol (RSD=26.3%), with a range of 0.5 mol/mol to 1.4 mol/mol.

Previous analysis identified a correlation between UFDF1 hold time and TSAC variability at BDS. Since the impact of the UFDF1 hold time, temperature, and protein concentration on TSAC decrease were not fully understood, additional temperature and protein concentration dependent data were collected at small scale to understand the impact on TSAC decrease during the UF1 hold. A multivariate evaluation of the three factors during UFDF1 hold was accomplished using a full factorial experimental study design evaluating a range for each factor (Table 6). This small scale characterization study design was executed using harvest from three batches (A, B, and C). Following small scale UFDF 1 operations for each harvest, UFDF1 pools were held at various hold times, temperatures, and protein concentrations (Table 6). Samples were purified using small scale Protein A column for TSAC analysis. The TSAC at Protein A pool was compared to the TSAC value at HCCF for the respective harvest and the total decrease in TSAC from HCCF (TSAC drop) was calculated for each UF1 hold condition.

TABLE 6

| Parameter/Attribute | Studied Characterization Range |
| --- | --- |
| Hold Temperature (° C.) | 15-25 |
| Hold Time (hours) | 0-60 |
| Protein Concentration (g/L) | 1.8-5.3 |

Figure 11:
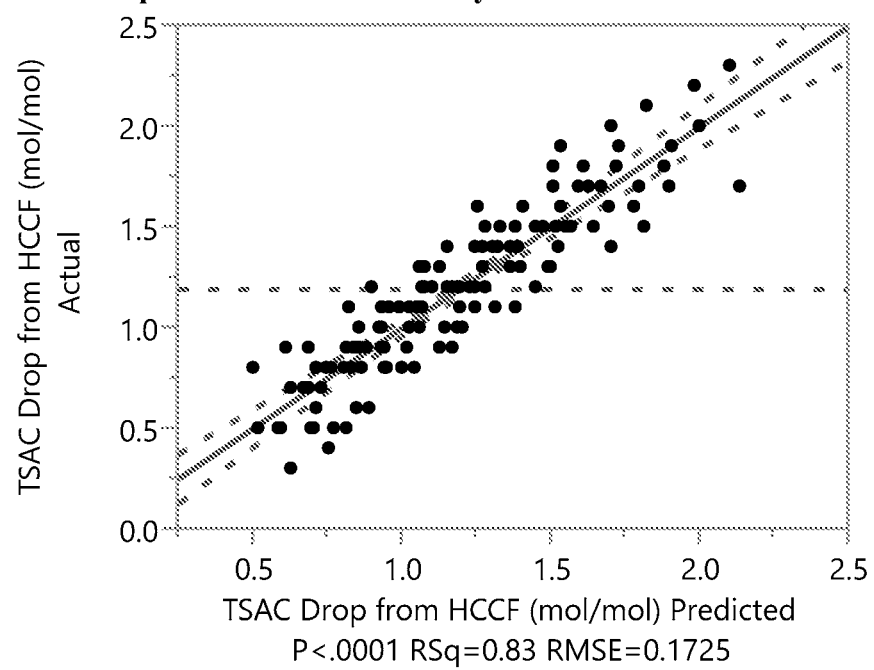
FIG. 11 shows the TSAC drop from HCCF to using a JMP model created by performing fit model analysis. Also included are the actual experimental results.
Figure 12:
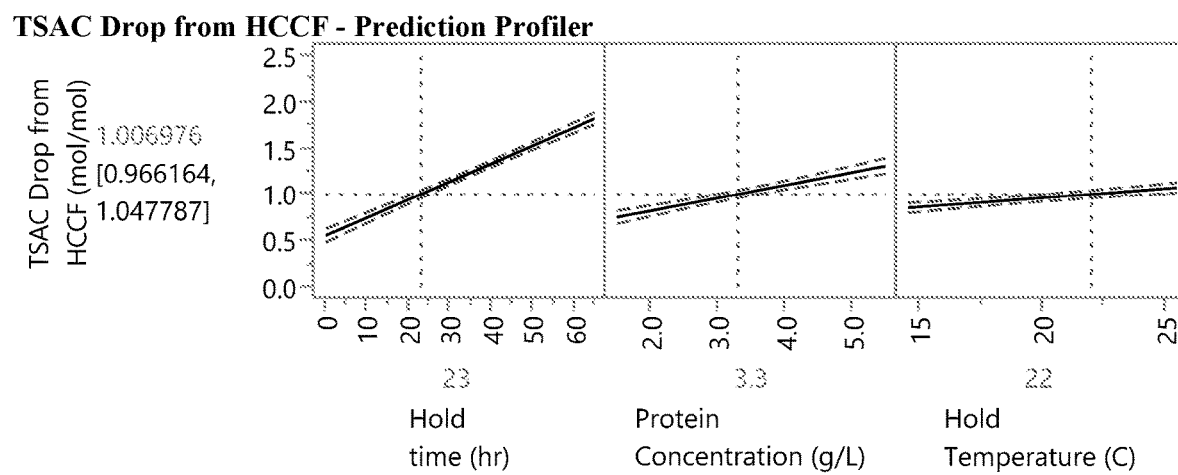
FIG. 12 includes the JMP model prediction profiler outputs for hold time, protein concentration, and hold temperature as a function of TSAC drop from HCCF.

A JMP model was created by performing fit model analysis on the TSAC drop during UFDF1 hold as per the experimental results. Each factor (hold time, temperature, and protein concentration) was included in a factorial analysis using the stepwise regression. Model outputs included the actual by predicted plot (FIG. 11), sorted parameter estimates, prediction expression, and prediction profiler (FIG. 12). The prediction expression was derived from the parameter estimates and was plotted in the prediction profiler.

To ensure that the small scale UFDF1 model as well as the JMP model created from these data are representative of large scale process, the predictive model was verified for its ability to predict BDS TSAC for 35 manufactured batches where HCCF TSAC and UFDF1 hold data (average hold time, protein concentration, and average hold temperature) are both available. For each manufactured batch, the predicted TSAC drop was subtracted from the measured HCCF TSAC to yield predicted ProA TSAC. Based on an average 0.2 mol/mol TSAC increase from ProA to BDS, the predicted BDS TSAC was calculated. The BDS TSAC was predictable within assay variability (±20%) for all manufacturing batches with the exception of batch # B.

Characterization studies demonstrated that UFDF 1 protein concentration has a statistically significant (p-value<0.0001) impact on TSAC decrease during UFDF1 hold. The TSAC decrease during UF1 hold is believed to occur due to presence of sialidase enzyme which is known to be present in mammalian cell culture harvest (Gramer and Goochee, *Biotechnol. Prog.* 9:366-373 (1993), incorporated specifically herein by reference). The protein concentration of asfotase alfa is considered a surrogate for concentration of sialidase enzyme during UFDF1 hold. However, this attribute was not defined for TSAC control in the drug substance manufacturing process.

In conclusion, the data suggests reducing the range of the hold time of the UFDF from 14-48 hours to 14-42 hours. Additionally, the data suggested adding a new performance attribute for protein concentration at the UFDF hold step with the range 2.0-4.3 g/L.

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the instant disclosure will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

What is claimed is:

1. A method of producing recombinant alkaline phosphatase comprising:
(I) (a) inoculating Chinese Hamster Ovary (CHO) cells expressing recombinant alkaline phosphatase;
(b) culturing the CHO cells in culture medium;
(c) isolating the recombinant alkaline phosphatase from the culture medium by at least one purification step to form harvest clarified culture fluid (HCCF) with a total sialic acid content (TSAC) of about 2.1 mol/mol to about 4.3 mol/mol;
(d) performing at least one additional protein purification step to form a filtration pool (UFDF), wherein the UFDF is held at a temperature of about 13° C. to about 27° C. for about 14 hours to about 42 hours, and at a protein concentration of about 2.0 g/L to about 4.3 g/L to reduce TSAC loss; and
(e) subjecting the UFDF to at least one chromatography step to obtain partially purified recombinant alkaline phosphatase; and
(f) recovering the recombinant alkaline phosphatase from the UFDF, wherein the recombinant alkaline phosphatase has a TSAC of about 1.2 mol/mol to about 3.0 mol/mol; or
(II) (a) inoculating CHO cells expressing recombinant alkaline phosphatase;
(b) culturing the CHO cells in culture medium to produce a cell culture;

(c) adding a nutrient supplement to the culture medium;
(d) isolating the recombinant alkaline phosphatase from the culture medium by at least one purification step to form a filtration pool (Ultrafiltration/Diafiltration UFDF), wherein the UFDF is held at a temperature of about 13° C. to about 27° C. for about 14 hours to about 42 hours, and at a protein concentration of about 2.0 g/L to about 4.3 g/L to reduce TSAC loss; and
(e) recovering the recombinant alkaline phosphatase from the UFDF, wherein the recombinant alkaline phosphatase in the UFDF has a TSAC of about 1.2 mol/mol to about 3.0 mol/mol.

2. The method of claim 1, wherein the culture medium comprises sialidase and the sialidase is selectively removed from the culture medium, the HCCF, and/or the UFDF and/or an exogenous sialyltransferase is added to the culture medium, the HCCF, and/or the UFDF.

3. The method of claim 1, wherein:
(i) the culturing of the CHO cells in the culture medium is at a temperature of about 36° C. to about 38° C.;
(ii) the nutrient supplement is added to the culture medium at least one day after inoculation of CHO cells into the culture medium;
(iii) the nutrient supplement is added at more than 2 different times;
(iv) the culture medium is selected from the group consisting of serum-free medium; CD DG44 Medium; SFM4CHO Medium; and combinations thereof;
(v) the culturing of the CHO cells is in a 0.25 L to a 25,000 L bioreactor;
(vi) the temperature of the culture medium is decreased about 80 hours to about 120 hours after the inoculation;
(vii) step (d) of (I) or (II) occurs about 10 to about 14 days after inoculation;
(viii) the TSAC of the HCCF is about 2.2 mol/mol to about 3.6 mol/mol; and/or
(ix) the at least one additional purification step comprises at least one of harvest clarification, filtration, ultrafiltration, diafiltration, viral inactivation, affinity capture, and combinations thereof.

4. The method of claim 3, wherein:
(a) the culturing of the CHO cells in the culture medium is at a temperature of about 37° C.;
(b) the culturing of the CHO cells is in a 100 L to 25,000 L bioreactor;
(c) the TSAC of the HCCF is about 2.2 mol/mol to about 3.4 mol/mol; and/or
(d) the at least one additional purification step comprises ultrafiltration and/or diafiltration.

5. The method of claim 4, wherein the culturing of the CHO cells is in a 2000 L to 20,000 L bioreactor.

6. The method of claim 1, wherein:
(i) the UFDF is held at a temperature of about 14° C. to about 26° C.; and/or
(ii) the UFDF has an alkaline phosphatase concentration of about 3.3 g/L to about 4.1 g/L.

7. The method of claim 6, wherein:
(a) the UFDF is held at a temperature of about 15° C. to about 26° C.; and/or
(b) the UFDF has a protein concentration of about 3.1 g/L.

8. The method of claim 7, wherein one or more of:
(i) the UFDF is held at a temperature of about 15° C. to about 25° C.; and
(ii) the at least one additional chromatography step and/or the at least one additional protein purification step is performed to obtain recombinant alkaline phosphatase with a TSAC of about 1.4 mol/mol to about 2.6 mol/mol.

9. The method of claim 8, wherein one or more of:
(a) the UFDF is held at a temperature of about 19° C. to about 25° C.; and
(b) the UFDF is held for about 17 hours to about 34 hours.

10. The method of claim 9, wherein the UFDF is held for about 19 hours to about 33 hours.

11. The method of claim 10, wherein the UFDF is held for about 25 hours to about 38 hours.

12. The method of claim 11, wherein the UFDF is held for about 29 hours to about 35 hours.

13. The method of claim 1, wherein:
(i) the at least one chromatography step is protein affinity chromatography;
(ii) the at least one chromatography step is Protein A chromatography;
(iii) the at least one chromatography step comprises column chromatography;
(iv) the at least one chromatography step comprises hydrophobic interaction chromatography;
(v) the at least one additional protein purification step of (I) comprises an additional diafiltration;
(vi) the at least one chromatography step and/or the at least one additional protein purification step comprises hydrophobic interaction chromatography and/or at least one additional diafiltration step;
(vii) step (d) of (I) further comprises a viral inactivation step; and/or
(viii) step (e) of (I) or (II) further comprises at least one additional chromatography and/or purification step.

14. The method of claim 1, wherein the recombinant alkaline phosphatase comprises the structure of W-sALP-X-Fc-Y-Dn-Z, wherein
W is absent or is an amino acid sequence of at least one amino acid;
X is absent or is an amino acid sequence of at least one amino acid;
Y is absent or is an amino acid sequence of at least one amino acid;
Z is absent or is an amino acid sequence of at least one amino acid;
F c is a fragment crystallizable region;
Dn is a poly-aspartate, poly-glutamate, or combination thereof, wherein n=10 or 16; and
sALP is a soluble alkaline phosphatase.

15. The method of claim 14, wherein the recombinant alkaline phosphatase comprises asfotase alfa (SEQ ID NO: 1).

16. The method of claim 13, wherein the recombinant alkaline phosphatase obtained from the protein affinity chromatography is stored at about 2° C. to about 8° C.

17. The method of claim 1, wherein (I) further comprises:
(i) adding a nutrient supplement to the culture medium of (b) after inoculation; and/or
(ii) measuring recombinant alkaline phosphatase activity.

18. A recombinant alkaline phosphatase produced by the method of claim 1.

19. A filtration pool (UFDF) comprising recombinant alkaline phosphatase produced by the method of claim 1.

20. A composition comprising the recombinant alkaline phosphatase of claim 19, wherein the composition further comprises at least one pharmaceutically acceptable carrier, diluent, or excipient or a combination thereof.

21. The method of claim 1, wherein in step (d) of (I), the UFDF is held at a temperature of 13° C. to 27° C. for 14 hours to 42 hours, and at a protein concentration of 2.0 g/L to 4.3 g/L to reduce the TSAC loss.

22. The method of claim 1, wherein in step (d) of (II), the UFDF is held at a temperature of 13° C. to 27° C. for 14 hours to 42 hours, and at a protein concentration of 2.0 g/L to 4.3 g/L to reduce the TSAC loss.

\* \* \* \* \*

UNITED STATES PATENT AND TRADEMARK OFFICE
CERTIFICATE OF CORRECTION

PATENT NO. : 11,913,039 B2
APPLICATION NO. : 17/043464
DATED : February 27, 2024
INVENTOR(S) : Rahul Godawat et al.

Page 1 of 1

It is certified that error appears in the above-identified patent and that said Letters Patent is hereby corrected as shown below:

In the Claims

Column 48, Claim 14, Line 44, replace "F c" with -- Fc --.

Signed and Sealed this
Third Day of September, 2024

Katherine Kelly Vidal
Director of the United States Patent and Trademark Office

SEQUENCE LISTING

```
<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
        50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415
```

-continued

```
Val Asp Tyr Ala His Asn Asn Tyr Gln Ala Gln Ser Ala Val Pro Leu
            420             425             430

Arg His Glu Thr His Gly Gly Glu Asp Val Ala Val Phe Ser Lys Gly
        435             440             445

Pro Met Ala His Leu Leu His Gly Val His Glu Gln Asn Tyr Val Pro
    450             455             460

His Val Met Ala Tyr Ala Ala Cys Ile Gly Ala Asn Leu Gly His Cys
465             470             475             480

Ala Pro Ala Ser Ser Leu Lys Asp Lys Thr His Thr Cys Pro Pro Cys
            485             490             495

Pro Ala Pro Glu Leu Leu Gly Gly Pro Ser Val Phe Leu Phe Pro Pro
            500             505             510

Lys Pro Lys Asp Thr Leu Met Ile Ser Arg Thr Pro Glu Val Thr Cys
            515             520             525

Val Val Val Asp Val Ser His Glu Asp Pro Glu Val Lys Phe Asn Trp
530             535             540

Tyr Val Asp Gly Val Glu Val His Asn Ala Lys Thr Lys Pro Arg Glu
545             550             555             560

Glu Gln Tyr Asn Ser Thr Tyr Arg Val Val Ser Val Leu Thr Val Leu
            565             570             575

His Gln Asp Trp Leu Asn Gly Lys Glu Tyr Lys Cys Lys Val Ser Asn
            580             585             590

Lys Ala Leu Pro Ala Pro Ile Glu Lys Thr Ile Ser Lys Ala Lys Gly
            595             600             605

Gln Pro Arg Glu Pro Gln Val Tyr Thr Leu Pro Pro Ser Arg Glu Glu
            610             615             620

Met Thr Lys Asn Gln Val Ser Leu Thr Cys Leu Val Lys Gly Phe Tyr
625             630             635             640

Pro Ser Asp Ile Ala Val Glu Trp Glu Ser Asn Gly Gln Pro Glu Asn
            645             650             655

Asn Tyr Lys Thr Thr Pro Pro Val Leu Asp Ser Asp Gly Ser Phe Phe
            660             665             670

Leu Tyr Ser Lys Leu Thr Val Asp Lys Ser Arg Trp Gln Gln Gly Asn
            675             680             685

Val Phe Ser Cys Ser Val Met His Glu Ala Leu His Asn His Tyr Thr
            690             695             700

Gln Lys Ser Leu Ser Leu Ser Pro Gly Lys Asp Ile Asp Asp Asp Asp
705             710             715             720

Asp Asp Asp Asp Asp Asp
            725
```